United States Patent

Lafon et al.

[11] 4,156,011
[45] May 22, 1979

[54] SULPHUR- AND OXYGEN-CONTAINING DIARYL COMPOUNDS

[75] Inventors: Victor Lafon; Louis Lafon, both of Paris, France

[73] Assignee: Societe Anonyme dite: Laboratoire L. Lafon, Maisons-Alfort, France

[21] Appl. No.: 784,940

[22] Filed: Apr. 5, 1977

Related U.S. Application Data

[63] Continuation-in-part of Ser. No. 739,359, Nov. 5, 1976, abandoned, which is a continuation of Ser. No. 617,675, Sep. 29, 1975, abandoned.

[30] Foreign Application Priority Data

Sep. 30, 1974 [GB] United Kingdom ............... 42387/74
Jan. 14, 1975 [GB] United Kingdom ................. 1587/75

[51] Int. Cl.$^2$ .......................................... A61K 31/235
[52] U.S. Cl. .................................... 424/309; 562/472;
562/427; 544/168; 568/637; 544/158; 544/174;
544/174; 424/244; 544/391; 424/248.57;
424/248.5; 544/159; 424/250; 424/267;
544/162; 424/273 R; 424/274; 544/394;
424/303; 424/308; 544/398; 424/317; 424/326;
260/239 B; 424/330; 424/335; 260/326.5 S;
424/340; 548/353; 260/326.84; 260/456 P;
260/501.2; 260/564 R; 260/558 S; 260/559 D;
260/570.5 S; 260/570.7; 260/607 AR; 260/609
R; 260/326.5 SF; 260/326.5 E; 260/326.5 L;
546/232; 546/226; 546/234; 560/9; 560/11;
560/17; 560/62; 560/63; 562/429; 562/431

[58] Field of Search ................. 560/9, 11, 63; 424/309

[56] References Cited

U.S. PATENT DOCUMENTS 3,721,703  3/1973  Nahm et al. ...................... 260/471 R
3,954,442  5/1976  Becker et al. ............................ 560/9

FOREIGN PATENT DOCUMENTS 2355115  5/1974  Fed. Rep. of Germany .............. 560/9
2547572  2/1977  Fed. Rep. of Germany ............. 560/63

OTHER PUBLICATIONS

Rousselet, Chem. Abst. 77:96726e (1972).
Rassous, Chem. Abst. 77:96889k (1972).
Debray, Chem. Abst. 77:96890d (1972).

*Primary Examiner*—Bernard Helfin
*Assistant Examiner*—Michael Shippen

[57] ABSTRACT

The sulphur- and oxygen-containing diaryl compounds of the formula:

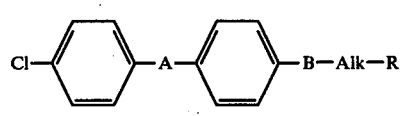

I in which A and B, which may be the same or different, represent O, S, SO or $SO_2$, Alk is a $C_1$–$C_4$ hydrocarbon radical with a straight or branched chain, R represents COOH, an esterified COOH group, a carboxylic amide group, OH, O-$SO_2CH_3$, $NH_2$, $NHR_1$, $NR_1R_2$, NHZOH, $NHZNR_1R_2$, C(=NH)$NH_2$, C(=NH)NHOH or 2-$\Delta^2$-imidazolinyl, Z is a $C_2$–$C_4$ hydrocarbon radical with a straight or branched chain, and $R_1$ and $R_2$ each represent a $C_1$–$C_3$ lower alkyl group, or together form, with the nitrogen atom to which they are linked, a N-heterocyclic group of 5 to 7 ring atoms which can be substituted and can comprise a second hetero-atom, and their addition salts with bases when R is COOH, and their addition salts with acids when R is a basic radical, are useful pharmacological agents in the treatment of circulatory complaints such as cardio-vascular illnesses.

5 Claims, No Drawings

SULPHUR- AND OXYGEN-CONTAINING DIARYL COMPOUNDS

CROSS REFERENCES

This application is a continuation-in-part of our application Ser. No. 739,359 filed Nov. 5, 1976, which is a continuation of our application Ser. No. 617,675 filed Sept. 29, 1975, both now abandoned.

The present invention relates to sulphur- and oxygen-containing diaryl compounds, their preparation and their application in therapy.

The present invention provides the sulphur- and oxygen-containing diaryl compounds of the formula:

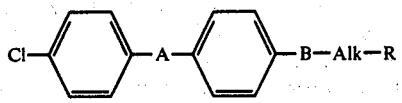
I in which A and B, which may be the same or different, represent O, S, So or $SO_2$, Alk is a $C_1$–$C_4$ hydrocarbon radical with a straight or branched chain, R represents COOH, an esterified COOH group, a carboxylic amide group, OH, O-$SO_2CH_3$, $NH_2$, $NHR_1$, $NR_1R_2$, NHZOH, $NHZNR_1R_2$, $C(=NH)NH_2$, $C(=NH)NHOH$ or 2-$\Delta^2$-imidazolinyl, Z is a $C_2$–$C_4$ hydrocarbon radical with a linear or branched chain, and $R_1$ and $R_2$ each represent a $C_1$–$C_3$ lower alkyl group, or together form, with the nitrogen atom to which they are linked, a N-heterocyclic group of 5 to 7 ring atoms which can comprise a second hetero-atom such as O and N and can be substituted, and their addition salts with bases if R is COOH, and with acids if R is $C(=NH)NH_2$, $C(=NH)NHOH$ or 2-$\Delta^2$-imidazolinyl or contains an amine group.

In the text which follows, the generic term "amidine" is to be understood to include not only the group $C(=NH)NH_2$ but also the amidoxime group $C(=NH)NHOH$ and cyclic amidine groups such as the 2-$\Delta^2$-imidazolinyl group.

The term "Alk" represents in particular the groups $CH_2$, $CH(CH_3)$, $C(CH_3)_2$, $CH_2CH_2$, $CH(CH_3)CH_2$, $C(CH_3)_2CH_2$, $CH_2CH(CH_3)$ or $CH_2C(CH_3)_2$. The group Z is in particular, $CH_2CH_2$, $CH(CH_3)CH_2$, $C(CH_3)_2CH_2$, $CH_2CH(CH_3)$ or $CH_2C(CH_3)_2$.

The expression "esterified COOH group" is to be understood to mean any group COOX, wherein X is either a $C_1$–$C_3$ lower alkyl group (such as methyl, ethyl, propyl or isopropyl) or a $CH_2CH_2NR_1R_2$ group (wherein $NR_1R_2$ is defined as above) or an ester radical which results from the esterification of a bis-[(S-hydroxyalkyl)thio]-alkane as in British specification No. 1,307,227.

Among the acid addition salts of the acids of the formula I (R=COOH) are included first the salts obtained with the usual organic bases and secondly the salts obtained with the bis-[(N-hydroxyalkyl)aminoalkylthio]-alkanes of the formula:

IX described in French Application No. 75/02,307 of 24th January 1975, wherein Bo is a $C_2$–$C_4$ hydroxyalkyl group or $C_2$–$C_4$ dihydroxyalkyl group, Ao is a $C_2$–$C_6$ alkylene group, Ro is H, alkyl, acyl or Bo and x is 0, 1 or 2.

The expression "carboxylic amide group" is to be understood to mean a group chosen from $CONH_2$, $CONHR_1$, $CONR_1R_2$, CONHZOH and $CONHZNR_1R_2$, wherein $R_1$, $R_2$ and Z are defined as above, and the amides which result from the condensation of an acid of formula I (R=COOH), in the form of the acid chloride, with an amine of the above formula IX.

Among the N-heterocyclic groups $NR_1R_2$ included in the definition given above there may be mentioned the morpholino, pyrrolidino, piperidino, 4-methyl-piperidino, 4-methyl-piperazino, 4-p-chlorophenyl-piperazino and azepino groups. The preferred groups $NR_1R_2$ are the dimethylamino and diethylamino groups.

Preferred compounds according to the invention are:

(a) the acids of the formula:

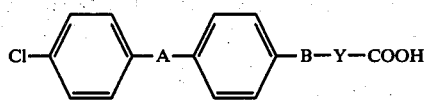
Ia in which A is O, S, SO or $SO_2$, B is O, S, SO or $So_2$, T is $CH_2$, $CH(CH_3)$ and $C(CH_3)_2$, and the addition salts obtained by reaction of the said acids with organic bases, especially with the bis[(N-hydroxyalkyl)aminoalkylthio]-alkanes of the formula IX mentioned above.

(b) The esters of the formula:

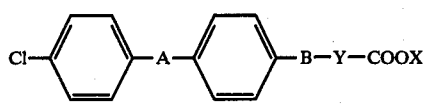
Ib wherein A is O, S, SO or $SO_2$, B is O, S, SO or $SO_2$, Y is $CH_2$, $CH(CH_3)$ and $C(CH_3)_2$ and X is defined as above, and their addition salts with acids, if X contains an amino group. Among the esters of the formula Ib are included the diesters of the formula

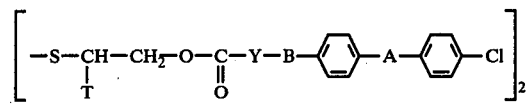

wherein n is an integer having a value of 5 to 15, preferably 10, T is H or $CH_3$, A, B and Y are defined as above. The preferred diesters are those in which A is O or S and B is O or S.

(c) the alcohols of the formula:

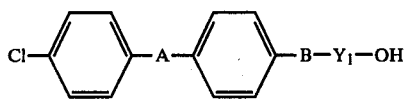
Ic wherein A is O, S, SO or $SO_2$, B is O, S, SO or $SO_2$, and $Y_1$ is $CH_2CH_2$, $CH(CH_3)CH_2$, $C(CH_3)_2CH_2$, $CH_2CH(CH_3)$ and $CH_2C(CH_3)_2$, and their derivatives resulting from the conversion of the OH group to an O-$SO_2CH_3$ group.

(d) The amides of the formula:

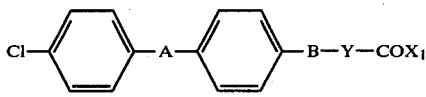

in which A is O, S, SO or SO$_2$, B is O, S, SO or SO$_2$, Y is CH$_2$, CH(CH$_3$) or C(CH$_3$)$_2$ and X$_1$ is NH$_2$, NHCH$_2$CH$_2$OH, NHCH$_2$CH$_2$N(CH$_3$)$_2$ or NHCH$_2$CH$_2$N(C$_2$H$_5$)$_2$, and their addition salts.

(e) The amines of the formula:

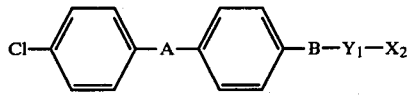

in which A is O, S, SO or SO$_2$, B is O, S, SO or SO$_2$, Y$_1$ is CH$_2$CH$_2$, CH(CH$_3$)CH$_2$, C(CH$_3$)$_2$CH$_2$, CH$_2$CH(CH$_3$) or CH$_2$C(CH$_3$)$_2$, and X$_2$ is NH$_2$, NHCH$_2$CH$_2$OH, NHCH(CH$_3$)CH$_2$OH, NHC(CH$_3$)$_2$CH$_2$OH, NHCH$_2$CH$_2$N(CH$_3$)$_2$, NHCH$_2$CH$_2$N(C$_2$H$_5$)$_2$, N(CH$_3$)$_2$, N(C$_2$H$_5$)$_2$ or NHCH(CH$_3$)$_2$, and their addition salts.

(f) The amidines of the formula:

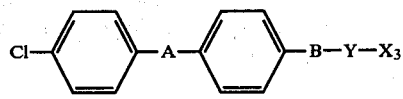

in which A is O, S, SO or SO$_2$, B is O, S, SO or SO$_2$, Y is CH$_2$, CH(CH$_3$) and C(CH$_3$)$_2$ and X$_3$ is C(=NH)NH$_2$, C(=NH)NHOH and 2-Δ$^2$-imidazolinyl and their addition salts.

The compounds of the formula I may be prepared by the two methods described below with their variants, where appropriate.

Method A

A diphenyl derivative of the formula:

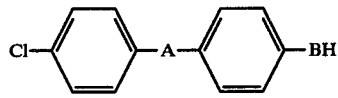

wherein A and B are defined as above, is reacted with a halogen derivative of the formula:

Hal-Alk-R'    III wherein Hal is a bromine or chlorine atom and R' is COOC$_2$H$_5$, OH, NH$_2$, NHR$_1$, NR$_1$R$_2$, NHZOH, NHZNR$_1$R$_2$ and CN, so as to give a compound of the formula:

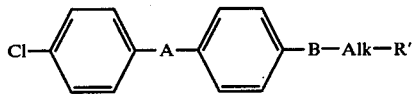

Thereafter, if necessary (a) the carboxylate (IV, R'=COOC$_2$H$_5$) is converted to the corresponding acid derivative (I, R=COOH) by hydrolysis, the said acid derivative thereafter being subjected, where appropriate, to amidification and esterification reactions to give the amides and the other esters;

(b) the alcohol (IV, R'=OH) is converted to the corresponding mesylate derivative (I, R=O-SO$_2$CH$_3$) by reaction with methanesulphonyl chloride; and (c) the cyano derivative (IV, R'=CN) is converted to the corresponding "amidine" derivative [I, R=C(=NH)NH$_2$, C(=NH)NHOH and 2-Δ$^2$-imidazolinyl] by reacting the said cyano derivative with, respectively, NH$_3$, NH$_2$OH and H$_2$NCH$_2$CH$_2$NH$_2$, in the presence of an alcohol.

To carry out the reaction II + III it is preferred to use a bromine derivative (III, Hal=Br) if R' is COOC$_2$H$_5$. Furthermore, if R' is CN, OH or amino, it is possible to use a chlorine or bromine derivative III, the chlorine derivative generally giving better yields than the bromine derivative in this case.

Amongst the variants of method A there may be mentioned:

the production of amines by reduction of the corresponding amides;

the production of amines from alcohols or the mesylates (R=O-SOCH$_3$) of the latter;

the production of other esters by transesterification of the compound IV (R'=COOC$_2$H$_5$);

the production of amides from the ester IV (R'=COOC$_2$H$_5$) by reaction with amines;

the direct production of amides by reaction of II with a bromo-alkylamide of the formula III (R'=carboxamido);

the production of the alcohol by reduction of the corresponding acid R=COOH;

the oxidation of the sulphide group A=S to the sulphinyl group A=SO and to the sulphonyl group A=SO$_2$, by oxidation of the said sulphide by H$_2$O$_2$ in the presence of acetic acid; this oxidation is carried out in accordance with a method which is in itself known, and for this purpose it is recommended to carry out the reaction at a temperature below, or equal to, 50° C. to obtain the sulphinyl derivative and at a temperature above 55° C. (55° C. to 100° C.) to obtain the sulphonyl derivative, using concentrated hydrogen peroxide of at least 110 volumes strength (that is to say water containing at least 33% by weight of hydrogen peroxide); the oxidation by means of H$_2$O$_2$ can be carried out at any stage of method A.

Method B

Method B, which is less general than the preceding method, comprises the reaction of a cuprous salt of the formula:

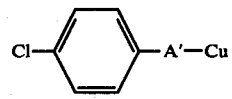

wherein A' is O or S, with a bromine derivative of the formula:

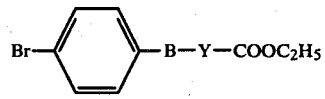

in which B is O or S, and Y is CH$_2$, CH(CH$_3$) or C(CH$_3$)$_2$ to give an ester of the formula:

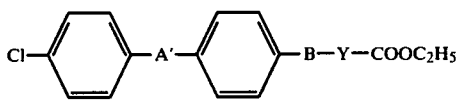

VII which is hydrolysed to give the corresponding acid

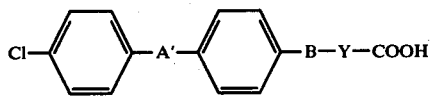

VIII

The acid of formula VIII is thereafter, where appropriate, subjected to the following reactions:

reduction of the acid to the corresponding alcohol, followed by treatment of the said alcohol, if necessary, with Cl-O-SO₂-CH₃, to give the corresponding mesylate, esterification of the acid to give the other esters;

amidification of the acid to give the amides, followed by reduction of the said amides, if necessary, to give the corresponding amines; and if appropriate, oxidation of the sulphide group A' and B=S to the sulphinyl group SO and the sulphonyl group SO₂ by means of H₂O₂, as indicated above.

Amongst the variants of method B there may be mentioned the trans-esterification and amidification of the ester VII.

The addition salts with acids, which can be prepared from the bases of the formula I, are obtained by methods in themselves known, for example by reaction of the free base with an inorganic or organic acid. Amongst the acids which can be used there may especially be mentioned hydrochloric, hydrobromic, hydriodic, sulphuric, formic, maleic, fumaric, oxalic, ascorbic, citric, acetic, methanesulphonic, p-toluenesulphonic, lactic, succinic, benzoic, salicylic, acetylsalicylic, malic, tartaric, glutamic and aspartic acid.

Some of the compounds of the invention are listed in Tables I and II below.

The compounds of the invention are useful in therapy in the treatment of circulatory complaints, especially cardio-vascular illnesses. Certain of them are hypo-lipidaemic agents and hypo-cholesterolaemic agents, certain of them are blood platelet anti-aggregation agents, and finally, others of them are simultaneously hypolipidaemic, hypo-cholesterolaemic and anti-aggregation agents, the property shared by all the compounds being a beneficial effect on circulatory complaints and in particular on cardio-vascular illnesses.

The invention includes within its scope therapeutic compositions comprising at least one compound of formula I as such or as one of its non-toxic addition salts in combination with a physiologically acceptable excipient.

TABLE I

Cl—⟨ ⟩—A—⟨ ⟩—B-Alk-R

| Example | Code No. | A | B | Alk | R | Melting point |
|---|---|---|---|---|---|---|
| 1 | — | S | O | C(CH₃)₂CH₂ | NH(CH₂)₂OH | 50° C. |
| 2(a) | CRL 40 238 | S | O | C(CH₃)₂CH₂ | NH(CH₂)₂OH | 148° C. |
| 3 | CRL 40 239 | SO₂ | O | C(CH₃)₂ | COOH | 135° C. |
| 4 | — | S | O | CH(CH₃) | COOC₂H₅ | (c) |
| 5 | CRL 40 246 | S | O | CH(CH₃) | COOH | 148° C. |
| 6 | CRL 40 248 | SO₂ | O | CH(CH₃) | COOH | 178° C. |
| 7 | CRL 40 251 | S | O | C(CH₃)₂ | CONH(CH₂)₂OH | 66° C. |
| 8 | CRL 40 386 | S | O | CH₂ | COOH | (b) |
| 9 | — | O | S | CH₂ | COOC₂H₅ | (c) |
| 10 | CRL 40 271 | O | S | CH₂ | COOH | 87° C. |
| 11 | CRL 40 272 | O | S | CH₂ | CONH(CH₂)₂OH | 98° C. |
| 12 | CRL 40 274 | O | S | CH₂CH₂ | NH(CH₂)₂OH | 67°–68° C. |
| 13 | — | O | S | C(CH₃)₂ | COOC₂H₅ | (c) |
| 14 | CRL 40 275 | O | S | C(CH₃)₂ | COOH | 131°–132° C. |
| 15 | CRL 40 276 | O | S | C(CH₃)₂CH₂ | OH | (c) |
| 16 | CRL 40 279 | O | S | C(CH₃)₂CH₂ | NH(CH₂)₂OH | <50° C. |
| 17 | CRL 40 201 | S | O | C(CH₃)₂ | COOH | 146°–148° C. |
| 18 | CRL 40 202 | SO | O | C(CH₃)₂ | COOH | 140°–142° C. |
| 19 | CRL 40 333 | O | O | CH₂ | COOH | 162° C. |
| 20 | CRL 40 299 | O | O | CH(CH₃) | COOH | 121° C. |
| 21 | CRL 40 308 | O | O | C(CH₃)₂ | COOH | 31° C. |
| 22 | CRL 40 281 | O | S | CH(CH₃) | COOH | 103° C. |
| 23 | CRL 40 293 | O | O | CH₂CH₂ | OH | 78° C. |
| 24 | CRL 40 310 | O | O | C(CH₃)₂CH₂ | OH | (c) |
| 25 | CRL 40 312 | O | O | C(CH₃)₂CH₂ | O—SO₂CH₃ | 85° C. |
| 26 | CRL 40 282 | O | S | CH(CH₃)CH₂ | OH | (c) |
| 27 | CRL 40 300 | O | O | CH(CH₃)CH₂ | OH | <50° C. |
| 28 | CRL 40 332 | O | O | CH₂C(CH₃)₂ | OH | 55° C. |
| 29(d) | CRL 40 317 | O | O | CH₂CH₂ | NH₂ | 215° C. |
| 30 | — | O | O | CH₂CH₂ | O—SO₂CH₃ | 68° C. |
| 31(d) | CRL 40 295 | O | O | CH₂CH₂ | NHCH₂CH₂OH | 141° C (e) |
| 32(d) | CRL 40 330 | O | O | CH₂CH₂ | N(C₂H₅)₂ | 119° C. |
| 33(d) | CRL 40 311 | O | O | C(CH₃)₂CH₂ | NHCH₂CH₂OH | 133° C. |
| 34 | — | O | O | CH(CH₃)CH₂ | O—SO₂HCH₃ | <50° C. |
| 35(d) | CRL 40 301 | O | O | CH(CH₃)CH₂ | NHCH₂CH₂OH | 145° C. |
| 36(d) | CRL 40 302 | O | O | CH(CH₃)CH₂ | NHC(CH₃)₂CH₂OH | 125° C. |
| 37 | CRL 40 283 | O | S | CH(CH₃)CH₂ | NHCH₂CH₂OH | (c) |
| 38 | CRL 40 309 | O | O | C(CH₃)₂ | CONHCH₂CH₂OH | 77° C. |
| 39(d) | CRL 40 334 | O | O | CH₂ | CONHCH₂CH₂N(C₂H₅)₂ | 120° C. |
| 40(d) | CRL 40 337 | O | O | CH₂ | C(=NH)NHOH | 148° C. (f) |

TABLE I-continued

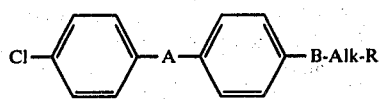

| Example | Code No. | A | B | Alk | R | Melting point |
|---------|----------|---|---|-----|---|---------------|
| 41(d) | CRL 40,338 | O | O | $CH_2$ | $C(=NH)NH_2$ | 166° C. |
| 42(d) | CRL 40,322 | O | O | $CH_2$ | 2-$\Delta^2$-imidazolinyle | 166° C.(g) |
| 12bis(h) | — | — | O | S | $CH_2CH_2$ | OH | 61° C. |
| 49 | CRL 40,351 | S | S | $CH(CH_3)$ | COOH | 71° C. |
| 50 | CRL 40,356 | S | S | $C(CH_3)_2$ | COOH | 140° C. |
| 51 | CRL 40,363 | S | S | $CH_2$ | COOH | 110° C. |

Notes :
(a) : This is the hydrochoride of Example 1;
(b) : the melting point is lower than 50° C.
(c) : oil
(d) : hydrochloride
(e) : the free base melts at 98° C.
(f) : the free base melts at 99° C.
(g) : the free base melts at 117° C.
(h) : described as an intermediate in Example 12

TABLE II $(CH_2)_{10}[-S-\underset{T}{\overset{|}{C}H}-CH_2-O-\underset{O}{\overset{\|}{C}}-Alk-B-\phantom{xx}-A-\phantom{xx}-Cl]_2$

| Example | Code No. | A | B | Alk | T | Melting point |
|---------|----------|---|---|-----|---|---------------|
| 52 | CRL 40,284 | O | S | $CH_2$ | H | 70–71° C. |
| 53 | CRL 40,368 | O | O | $C(CH_3)_2$ | H | (a) |
| 54 | CRL 40,374 | O | O | $C(CH_3)_2$ | $CH_3$ | (a) |
| 55 | CRL 40,377 | O | O | $CH(CH_3)$ | H | (a) |
| 56 | CRL 40,378 | O | O | $CH(CH_3)$ | $CH_3$ | (a) |
| 57 | CRL 40,379 | O | O | $CH_2$ | H | 59° C. |
| 58 | CRL 40,380 | O | O | $CH_2$ | $CH_3$ | 45° C. |
| 59 | CRL 40,387 | S | O | $C(CH_3)_2$ | $CH_3$ | (a) |
| 60 | CRL 40,388 | S | O | $CH_2$ | H | 72° C. |
| 61 | CRL 40,389 | S | O | $CH_2$ | $CH_3$ | 52° C. |
| 62 | CRL 40,390 | S | O | $CH(CH_3)$ | H | (a) |
| 63 | CRL 40,391 | S | O | $CH(CH_3)$ | $CH_3$ | (a) |
| 64 | CRL 40,394 | S | S | $CH_2$ | H | 55° C. |
| 65 | CRL 40,395 | S | S | $CH_2$ | $CH_3$ | <40° C. |
| 66 | CRL 40,398 | S | S | $CH(CH_3)$ | H | (a) |
| 67 | CRL 40,399 | S | S | $CH(CH_3)$ | $CH_3$ | (a) |
| 68 | CRL 40,402 | S | S | $C(CH_3)_2$ | H | (a) |
| 69 | CRL 40,403 | S | S | $C(CH_3)_2$ | $CH_3$ | (a) |
| 70 | CRL 40,405 | O | S | $CH_2$ | $CH_3$ | (a) |
| 71 | CRL 40,408 | O | S | $CH(CH_3)$ | H | (a) |
| 72 | CRL 40,409 | O | S | $CH(CH_3)$ | $CH_3$ | (a) |
| 73 | CRL 40,413 | O | S | $C(CH_3)_2$ | H | (a) |
| 74 | CRL 40,414 | O | S | $C(CH_3)_2$ | $CH_3$ | (a) |
| 75 | CRL 40,253 | S | O | $C(CH_3)_2$ | H | (a) |

Note
(a) = oil

Other advantages and characteristics of the invention will be better understood on reading the preparation examples which follow and are given by way of illustration but without implying any limitation. In these examples, the synthesis of the compounds II, V and VI, which can be used as the starting material according to the invention, has also been illustrated. Furthermore, it is obvious that the isomers (+) and (−) of the racemic compounds which have been described in the said examples can be isolated, in accordance with a method which is in itself known.

EXAMPLE 1

N-Hydroxyethyl-4-(4-chlorophenylthio)-phenoxy-isobutylamine, alternative nomenclature: N-hydroethyl-2-[4-(4-chlorophenylthio)-phenoxy]-2-methyl-1-propylamine

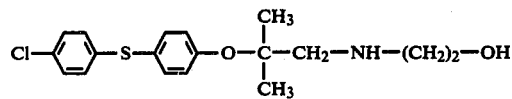

A solution of 21.6 g (0.075 mol) of sodium bis-(2-methoxy-ethoxy)-aluminium hydride in 50 ml of benzene is run over the course of 30 minutes into a refluxing solution of 18.3 g (0.050 mol) of N-hydroxyethyl-4-(4-chlorophenylthio)-phenoxy-isobutyramide (prepared as indicated later in Example 7) in 75 ml of benzene. The mixture is kept under reflux for 1 hour 30 minutes and is then hydrolysed with 100 ml of 4 N sodium hydroxide solution, whilst cooling. The organic phase is decanted, washed with water and extracted with dilute hydrochloric acid, and after rendering the aqueous phase alkaline with concentrated sodium hydroxide solution, 10.6 g of an orange product are obtained.

Instantaneous melting point (Köfler)=50° C.

EXAMPLE 2

N-Hydroxyethyl-4-(4-chlorophenylthio)-phenoxy-isobutylamine hydrochloride

Code No. CRL 40,238

10 g of the free base of Example 1, in ethyl acetate, are treated with a solution of hydrogen chloride in ether. After purification of the precipitate by recrystallisation from a mixture of ethyl acetate and ethanol (1:2), 8 g of a slightly beige powder which is insoluble in water are obtained.

Instantaneous melting point (Köfler)=148° C.

EXAMPLE 3

4-(4-chlorophenylsulphonyl)-phenoxy-isobutyric acid, alternative nomenclature
2-[4-(4-chlorophenylsulphonyl)phenoxy]-2-methyl-propionic acid

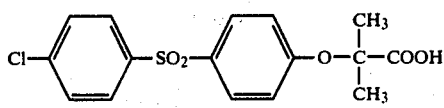

Code No. CRL 40,239

A solution of 10.75 g (0.033 mol) of p-(p-chlorophenylthio)-phenoxy-isobutyric acid (CRL 40,201) and of 10 ml (0.100 mol) of hydrogen peroxide of 120 volumes strength, in 50 ml of acetic acid, is heated at between 55° and 70° C. for 3 hours. Thereafter the greater part of the solvents is driven off under reduced pressure and the residue is dissolved in diethyl ether, which is washed with water. After evaporation of the solvent, the residual oil is solidified in petroleum ether and after filtration gives 10.7 g of a white powder which is insoluble in water and soluble in alcohol.

Instantaneous melting point (Kofler) = 135° C.
Yield = 91%.

EXAMPLE 4

Ethyl (±)-2-[4-(4-chlorophenylthio)-phenoxy]-propionate

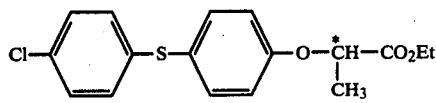

A mixture of 13.65 g (0.050 mol) of ethyl (±)-2-(4-bromophenoxy)-propionate and 11.6 g (0.056 mol) of cuprous p-chlorophenylthiolate in 100 ml of quinoline and 10 ml of anhydrous pyridine is heated to about 170° C. for 4 hours. Thereafter the reaction mixture is poured onto 175 g of ice and 58 ml of concentrated hydrochloric acid. After stirring overnight, the mixture is extracted with diethyl ether, which is washed successively with dilute hydrochloric acid and water and gives, after evaporation of the solvent, 16.75 g of an orange-coloured oil.

Yield ≈ 100%.

EXAMPLE 5

(±)-2-[4-Chlorophenylthio)-phenoxy]-propionic acid

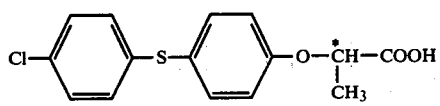

Code No. CRL 40,246

A solution of 16.7 g (about 0.05 mol) of the preceding ester and of 3 g (0.075 mol) of sodium hydroxide pellets in 50 ml of ethanol and 25 ml of water is heated to the reflux temperature for 1 hour. The ethanol is then driven off under reduced pressure and the residue is diluted with 75 ml of water. The aqueous phase is acidified with hydrochloric acid and extracted with diethyl ether, and the extract is then washed with water. The organic phase is in turn extracted with a solution of potassium bicarbonate, and after acidification and filtration this aqueous phase gives 12.4 g of a slightly grey powder. After purification of 12 g of this powder by crystallisation, and treatment with charcoal, in diisopropyl ether, 8.2 g of a white powder which is insoluble in water and soluble in alcohol are obtained.

Instantaneous melting point (Köfler) = 148° C.

EXAMPLE 6

(Code No. CRL 40,248)

On oxidising the acid of Example 5 (CRL 40,246) by means of $H_2O_2$ as described in Example 3, (±)-2-[4-(4-chlorophenylsulphonyl)-phenoxy]-propionic acid is obtained.

Instantaneous melting point (Köfler) = 178° C.

EXAMPLE 7

N-Hydroxyethyl-4-(4-chlorophenylthio)-phenoxy-isobutyramide, alternative nomenclature
N-hydroxyethyl-2-[4-(4-chlorophenylthio)-phenoxy]-2-methyl-1-propionamide

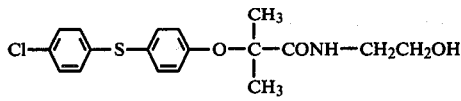

Code No. CRL 40,251

(a) p-(p-Chlorophenylthio)-phenoxy-isobutyroyl chloride

A mixture of 15 g (0.0465 mol) of p-(p-chlorophenylthio)-phenoxy-isobutyric acid (CRL 40,201) and of 16.75 ml (0.232 mol) of thionyl chloride is heated to the reflux temperature for 10 minutes. After having taken up the reaction mixture in benzene, filtered the solution in the presence of charcoal and evaporated the solvent, 16 g of an orange-coloured oil are obtained.

Yield = about 100%.

(b) CRL 40,251

A solution of 16 g (0.040 mol) of the preceding acid chloride in 25 ml of benzene is run over the course of 15 minutes into a suspension of 13.4 g (0.220 mol) of 2-aminoethanol in 30 ml of benzene at between 20° and 55° C. The reaction mixture is heated to the reflux temperature for 2 hours and is evaporated to dryness under reduced pressure. The residue is dissolved in ethyl acetate, which is washed successively with water, dilute hydrochloric acid and a solution of potassium carbonate. The oil obtained, after evaporation of the solvent, is purified by washing in diisopropyl ether (sic), giving 10.6 g of a powder which is insoluble in water.

Instantaneous melting point (Köfler) = 66° C.
Yield = 62.8%.

EXAMPLE 8 p-(p-Chlorophenylthio)-phenylthioacetic acid

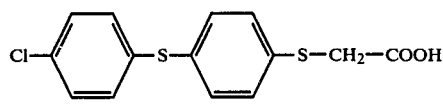

Code No.: CRL 40,386

(a) Copper p-chlorophenylthiolate

A mixture of 265 g (1.83 mols) of p-chlorothiophenol and 80 g (0.55 mol) of cuprous oxide which has been freshly prepared (by reaction of cupric acetate with glucose), in 1,500 ml of anhydrous ethanol, is heated under reflux for 24 hours. After filtering, and washing the precipitate with alcohol, 214 g of a yellow powder are obtained.

(b) Ethyl p-bromophenoxy-acetate 2.76 g of sodium are dissolved in 100 ml of anhydrous ethanol and 20.8 g (0.120 mol) of p-bromophenol are added. 22.1 g (0.132 mol) of ethyl bromoacetate are run into this solution over the course of 20 minutes and the mixture is then heated under reflux for 1 hour. The ethanol is driven off under reduced pressure and the residue is dissolved in diethyl ether; after washing with water and then with a potassium carbonate solution, and evaporating the solvent, 30.2 g of a white powder are obtained. After purification of this product by crystallisation from petroleum ether, 23 g of a white, water-insoluble powder are obtained.

Instantaneous melting point=below 50° C.
Yield=74%.

(c) Ethyl p-(p-chlorophenylthio)-phenoxy-acetate

A mixture of 21.9 g (0.0845 mol) of ethyl p-bromophenoxy-acetate and 20.7 g (0.1000 mol) of Cu p-chlorophenylthiolate (I) in 65 ml of quinoline and 21.5 ml of anhydrous pyridine is heated at about 170° C. for 6 hours. Thereafter the reaction mixture is poured onto 175 g of ice and 70 ml of concentrated hydrochloric acid. After having stirred the mixture for 2 hours at ambient temperature (15°–25° C.), the insoluble matter is extracted with diethyl ether, which is washed successively with dilute hydrochloric acid and with water, and after evaporation of the solvent gives 27.3 g of a red-brown oil.

Yield about 100%.

(d) CRL 40,386

A solution of 27.3 g ($\simeq$0.0845 mol) of the above product and of 7.1 g (0.1270 mol) of KOH pellets in 90 ml of ethanol and 45 ml of water is heated for 2 hours under reflux. The ethanol is then driven off under reduced pressure and the residue is diluted with 100 ml of water. The aqueous phase is acidified with concentrated hydrochloric acid, the insoluble matter is extracted with ethyl acetate and the organic phase obtained is washed with water and then dried over dry sodium sulphate. After evaporating the solvent, 24.7 g of a beige powder are obtained, and this is purified by recrystallisation from benzene. 19.5 g of CRL 40,386 are obtained.

Instantaneous melting point (Köfler)=155° C.
Yield of stage (d)=81%.
Overall yield=60%.

EXAMPLE 9

On reacting ethyl α-bromoacetate with p-(p-chlorophenoxy)-thiophenol in accordance with the process described in Example 13 below, ethyl 4-(4-chlorophenoxy)-phenylthioacetate is obtained in the form of an oil.

EXAMPLE 10

4-(4-Chlorophenoxy)-phenylthioacetic acid

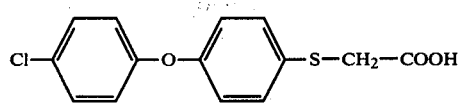

Code No. CRL 40,271

Hydrolysis of the product of Example 9 in accordance with the working method described in Example 14 gives 4-(4-chlorophenoxy)-phenylthioacetic acid.

Instantaneous melting point (Köfler)=87° C.

EXAMPLE 11

N-Hydroxyethyl-4-(4-chlorophenoxy)-phenylthioacetamide

Code No. CRL 40,272

On subjecting the acid of Example 10 to an amidification reaction with 2-amino-ethanol in accordance with the working method described in Example 7, CRL 40,272 is obtained.

Instantaneous melting point (Köfler)=98° C.

EXAMPLE 12

N-Hydroxyethyl-2-[4-(4-chlorophenoxy)phenylthio]-ethylamine

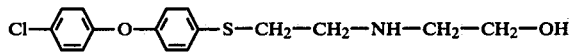

Code No. 40,274

(a) 2-[4-(4-Chlorophenoxy)phenylthio]-ethanol (Example 12 bis)

3 ml (0.030 mol) of 10 N sodium hydroxide solution are run over the course of 10 minutes into a solution of 6.85 g (0.029 mol) of 4-(4-chlorophenoxy)-thiophenol and 2.58 g (0.032 mol) of 2-chloroethanol in 20 ml of ethanol, at between 20° C. and 42° C. The mixture is stirred for 2 hours at ambient temperature and the solvent is then driven off under reduced pressure. After having dissolved the residue in diethyl ether, washed the organic phase obtained with dilute sodium hydroxide solution and water and then evaporated the solvent, 7.9 g of a fragrant pink powder are obtained. This powder is purified by crystallisation from cyclohexane to give 6.6 g of a pale pink powder.

Instantaneous melting point (Köfler)=61° C.
Yield=81.2%.

(b) [4-(4-Chlorophenoxy)-phenylthio]-2-chloroethane 2 ml (0.0278 mol) of thionyl chloride are run over the course of 5 minutes into a solution of 6.5 g (0.0232 mol) of the preceding product in 15 ml of benzene and the mixture is then heated to the reflux temperature for 1 hour. The reaction mixture is then evaporated to dryness under reduced pressure and the residue is dissolved in diethyl ether. The organic phase obtained is washed with water and a potassium carbonate solution, dried over dry sodium sulphate and treated with charcoal, and the solvent is then evaporated to give 6.75 g of a white powder.

Instantaneous melting point (Köfler)=59° C.
Yield=97.2%.

(c) CRL 40,274

A mixture of 6.7 g (0.0224 mol) of the preceding product and of 6.85 g (0.112 mol) of 2-amino-ethanol is heated slowly to 170° C. (over the course of 30 minutes). Thereafter the reaction mixture is taken up in chloroform and the chloroform solution is washed successively with water, dilute sodium hydroxide solution and water. After drying, and evaporating the solvent, 7.05 g of an oil which crystallises are obtained. 6.8 g of this product are purified by two successive crystallisations from diisopropyl ether to give 4.8 g of a white powder which is insoluble in water.

Instantaneous melting point (Köfler)=67°–68° C.
Yield of stage c=70%.

EXAMPLE 13

Ethyl 4-(4-chlorophenoxy)-phenylthio-isobutyrate, alternative nomenclature:ethyl 2-[4-(4-chlorophenoxy)-phenylthio]-2-methyl-propionate 9.05 g (0.0464 mol) of ethyl α-bromoisobutyrate are run over the course of 15 minutes, at about 60° C., into a solution of 10 g (0.0422 mol) of p-(p-chlorophenoxy)-thiophenol and 1 g (0.0422 mol) of sodium in 40 ml of anhydrous ethanol. The mixture is stirred for 1 hour at ambient temperature and is evaporated to dryness under reduced pressure. After having dissolved the residue in diethyl ether, and washed the organic phase obtained with water and dried it over dry sodium sulphate, the solvent is evaporated, to give 14.2 g of a limpid pale yellow oil.

Yield=96%.

EXAMPLE 14

4-(4-chlorophenoxy)-phenylthio-isobutyric acid, alternative nomenclature:
2-[4-(4-chlorophenoxy)-phenylthio]-2-methyl-propionic acid

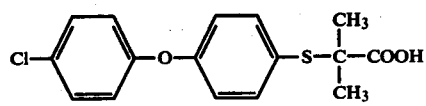

Code No. CRL 40,275

A solution of 14 g (0.04 mol) of the ester of Example 13 and of 3.36 g (0.06 mol) of potassium hydroxide pellets in 20 ml of water and 40 ml of ethanol is heated to the reflux temperature for 1 hour. The ethanol is evaporated under reduced pressure and the residue is diluted with 50 ml of water. The solution is acidified to Congo Red and the insoluble matter is extracted with diethyl ether. The organic phase obtained is in turn extracted with a potassium bicarbonate solution. After acidifying this aqueous phase with concentrated hydrochloric acid, 10 g of a white powder which is insoluble in water are isolated by extraction with diethyl ether.

Instantaneous melting point (Köfler)=131°–132° C.
Yield=77.5%.

EXAMPLE 15

4-(4-Chlorophenoxy)-phenylthio-isobutanol, alternative nomenclature:
2-[4-(4-chlorophenoxy)-phenylthio]-2-methyl-1-propanol

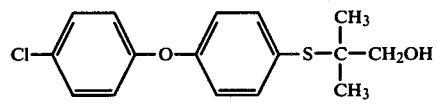

Code No. CRL 40,276

A solution of 9 g (0.0279 mol) of p-(p-chlorophenoxy)-phenylthio-isobutyric acid (CRL 40,275) in 75 ml of diethyl ether and 7.5 ml of tetrahydrofurane is run over the course of 30 minutes into a suspension of 2.4 g (0.0617 mol) of lithium aluminium hydride in 20 ml of diethyl ether and the mixture is then stirred for 1 hour at the reflux temperature. The excess hydride is neutralised with ethyl acetate and the product is hydrolysed with a dilute hydrochloric acid solution, whilst cooling. After washing the organic phase obtained with water and dilute sodium hydroxide solution, drying it and evaporating the solvent, 8.6 g of a limpid pale yellow oil are obtained.

Yield: about 100%.

EXAMPLE 16

N-Hydroxyethyl-4-(4-chlorophenoxy)phenylthio-isobutylamine, alternative nomenclature:
N-hydroxyethyl-2-[4(4-chlorophenoxy)-phenylthio]-2-methyl-1-propylamine

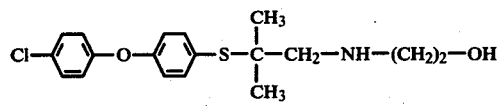

Code No. CRL 40,279

2.25 ml (0.0311 mol) of thionyl chloride are run over the course of 5 minutes into a solution of 8 g (0.0259 mol) of p-(chlorophenoxy)phenylthio-isobutanol (CRL 40,276) in 30 ml of anhydrous benzene and 0.5 ml of anhydrous pyridine. The mixture is heated to the reflux temperature for 30 minutes and is evaporated to dryness under reduced pressure. After dissolving the residue in diethyl ether, washing the ether solution with water and drying it over dry sodium sulphate, and evaporating the solvent, 8.05 g of 4-(4-chlorophenoxy)-phenylthio-isobutyl chloride are obtained in the form of a limpid orange-yellow oil.

Yield=95.2%.

A mixture of 8 g (0.024 mol) of the preceding product and 7.35 g (0.120 mol) of 2-amino-ethanol is generally heated to 170° over the course of 30 minutes. The reaction mixture is taken up in diethyl ether, which is washed with water. The organic phase is extracted with a dilute hydrochloric acid solution, which is in turn rendered alkaline to permit the extraction of 6.85 g of a pale yellow oil which is insoluble in water and crystallises on cooling.

Melting point <50° C.
Yield=81.5%
Total yield=77.5%.

EXAMPLE 17

4-(4-Chlorophenylthio)-phenoxyisobutyric acid, alternative nomenclature:
2-[4-(4-chlorophenylthio)-phenoxy]-2-methylpropionic acid

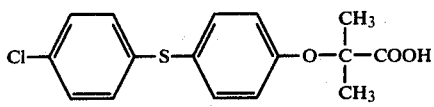

Code No. CRL 40,201

23.8 g (0.115 mol) of cuprous 4-chlorophenylthiolate (p-Cl-C$_6$H$_4$-S-Cu) are added to a solution of 28.7 g (0.1 mol) of ethyl 4-bromophenoxy-isobutyrate in 75 ml of quinoline and 25 ml of pyridine. The mixture is heated to 170° C. whilst stirring for 3 hours. The solution is poured into ice containing 80 ml of concentrated HCl, the mixture is stirred for 1 hour and extracted with ethyl acetate, the extract is washed with water and then with dilute bicarbonate and is dried, and the ethyl acetate is driven off in vacuo. The oil thus obtained is dissolved in 120 ml of ethanol and is treated for 1 hour, at the reflux temperature, with 6 g (0.15 mol) of NaOH pellets in 75 ml of water. The ethanol is evaporated in vacuo, 200 ml of water are added to the residue and the acid is precipitated by means of concentrated HCl. It is filtered off, washed with water, dried and recrystallised from diisopropyl ether. CRL 40,201 is obtained in a yield of 56%.

Melting point = 146°–148° C.

EXAMPLE 18

4-(4-Chlorophenylsulphinyl)-phenoxyisobutyric acid, alternative nomenclature
2-[4-(4-chlorophenylsulphinyl)-phenoxy]-2-methylpropionic acid

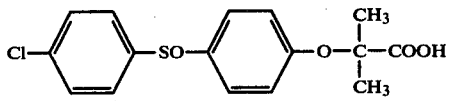

Code No. CRL 40, 202

6.45 g (0.02 mol) of 4-(4-chlorophenylthio)-phenoxyisobutyric acid dissolved in 25 ml of acetic acid are oxidised with 2 ml (0.02 mol) of hydrogen peroxide of 110 volumes strength. The mixture is heated for 1 hour at 50° C. and is evaporated to dryness in vacuo, and the residue is taken up in diisopropyl ether, filtered off and recrystallised from ethyl acetate. This gives CRL 40,202 in a yield of 86%.

Melting point = 140°–142° C.

EXAMPLE 19

4-(4-Chlorophenoxy)-phenoxyacetic acid

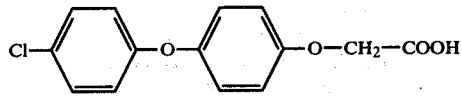

Code No. CRL 40,333

(a) p-Bromoanisole 25 g (0.20 mol) of dimethyl sulphate are run over the course of 45 minutes into a refluxing suspension of 34.4 g (0.20 mol) of p-bromophenol and 27.5 g (0.20 mol) of potassium carbonate in 150 ml of acetone. The reflux is maintained for a further hour, the inorganic salts are removed by filtration and the filtrate is evaporated to dryness under reduced pressure. The residue is dissolved in diethyl ether, the ether solution is washed with dilute sodium hydroxide solution and water and is dried over dry sodium sulphate, and the solvent is evaporated to give 37.2 g of a slightly yellow oil which is insoluble in water.

Yield = 99.5%

Boiling point/13 mm Hg = 95° C.

(b) p-(p-Chlorophenoxy)-anisole

A mixture of 67 g (0.520 mol) of p-chlorophenol and 29.5 g (0.520 mol) of KOH pellets is heated to 100° C. for 2 hours under a pressure of about 5 mm Hg. Thereafter 117 g (0.625 mol) of p-bromoanisole and 1 g of copper powder are added and the mixture is then heated to about 220°–230° C. for 5 hours. The cooled reaction mixture is taken up in diethyl ether and after removing the inorganic salts by filtration the filtrate is washed with 2 N sodium hydroxide solution and with water. The solvent is driven off under reduced pressure, drying is carried out with sodium sulphate and 133 g of an orange-coloured oil are obtained. Purification of this oil by distillation under reduced pressure given 70 g of a white crystalline mass which is insoluble in water.

Boiling point/2-3 mm Hg = 150° C.

Yield = 57.3%.

(c) p-(p-Chlorophenoxy)-phenol

A solution of 69 g (0.294 mol) of the preceding product and of 265 ml of 48% strength hydrobromic acid in 630 ml of acetic acid is heated to the reflux temperature for 2 hours and is then evaporated to dryness under reduced pressure. The residue is dissolved in diethyl ether, which is washed successively with water and a potassium bicarbonate solution. After drying over dry sodium sulphate and evaporating the solvent of the organic phase, 64.7 g of a slightly beige powder are obtained. Purification of this powder by crystallisation from cyclohexane given 60.5 g of a white crystalline powder which is insoluble in water.

Instantaneous melting point (Köfler) = 82° C.

Boiling point/0.4 mm Hg = 143° C.

Yield = 93.5%.

(d) CRL 40,333

A solution of 7.1 g (0.075 mol) of chloroacetic acid in 20 ml of ethanol is run over the course of 30 minutes into a solution, kept at about 60° C., of 15 g (0.068 mol) of the preceding product and 6.3 g (0.157 mol) of sodium hydroxide pellets in 50 ml of water. The mixture is heated to the reflux temperature for 2 hours, the ethanol is driven off under reduced pressure and the residue is acidified to Congo Red with dilute hydrochloric acid. The precipitate obtained is filtered off and dried. The purification of this precipitate by washing with hot diisopropyl ether gives 10 g of a slightly pink crystalline powder which is insoluble in water.

Instantaneous melting point (Köfler) = 162° C.

Yield of stage d) = 53%

Total yield = 21.2%.

EXAMPLE 20

(±)-2-[4-(4-Chlorophenoxy)-phenoxy]-propionic acid

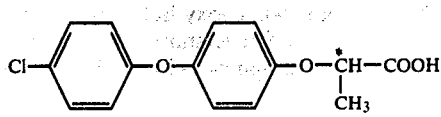

Code No. CRL 40,299

(a) Ethyl (±)-2-[4-(4-chlorophenoxy)-phenoxy]-propionate 20.9 g (0.115 mol) of ethyl 2-bromo-propionate are run over the course of 30 minutes into a hot solution of 23 g (0.1045 mol) of p-(p-chlorophenoxy)-phenol and 2.4 g (0.1045 mol) of sodium in 90 ml of anhydrous ethanol and the mixture is then heated to the reflux temperature for 2 hours. The inorganic salts are removed by filtration and the ethanol is driven off under reduced pressure. After having dissolved the residue in diethyl ether, washed the solution with water, dried the organic phase over dry sodium sulphate and evaporated the solvent, 32.5 g of an orange-coloured oil which is insoluble in water are obtained.

Yield 97%.

(b) CRL 40,299

A solution of 32 g (0.10 mol) of the preceding product and of 8.4 g (0.15 mol) of potassium hydroxide pellets in 100 ml of ethanol and 50 ml of demineralised water is heated to the reflux temperature for 2 hours. The ethanol is driven off under reduced pressure and the residue is taken up in water. The solution obtained is acidified to Congo Red and the insoluble matter is extracted with diethyl ether. The organic phase obtained is in turn extracted with a potassium bicarbonate solution. After acidifying this aqueous phase with concentrated hydrochloric acid, 25 g of a white powder which is insoluble in water are isolated by extraction with diethyl ether.

Instantaneous melting point (Köfler) = 121° C.
Yield of stage b) = 85.6%.

EXAMPLE 21

4-(4-Chlorophenoxy)-phenoxy-isobutyric acid, alternative nomenclature:
2-[4-(4-chlorophenoxy)-phenoxy]-2-methylpropionic acid

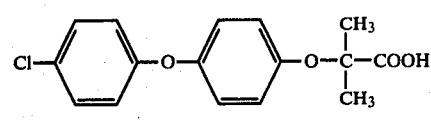

Code No. CRL 40,308

17.5 ml (0.1530 mol) of chloroform are run (over the course of 30 minutes) into a hot suspension of 25.9 g (0.1175 mol) of p-(p-chlorophenoxy)-phenol and 28.2 g (0.7050 mol) of sodium hydroxide pellets in 152 ml (2.3500 mols) of acetone and the reflux is then maintained for 4 hours. The reaction mixture is evaporated to dryness under reduced pressure, the residue is taken up in water and the mixture is acidified to Congo Red with concentrated hydrochloric acid. The insoluble matter is extracted with diethyl ether and the organic phase is in turn extracted with a potassium bicarbonate solution. Acidification of the aqueous phase with concentrated hydrochloric acid liberates a precipitate which is isolated by filtration. Purification of this precipitate by two successive crystallisations and treatment with charcoal (CXA) in cyclohexane gives 25.6 g of a slightly yellow powder which is insoluble in water.

Instantaneous melting point (Köfler) = 131° C.
Yield = 74%.

EXAMPLE 22

(±)-2-[4-(4-chlorophenoxy)-phenylthio]-propionic acid

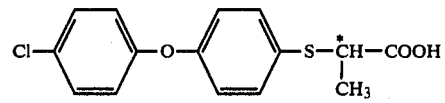

Code No. CRL 40,281

(a) p-(p-(Chlorophenoxy)-nitrobenzene 56 g (0.400 mol) of potassium carbonate and 5.6 g of purified copper are added to a lukewarm solution (≃60° C.) of 51.5 g (0.400 mol) of p-chlorophenol and 72 g (0.456 mol) of p-chloronitrobenzene in 40 ml of dimethylformamide and the mixture is then heated to the reflux temperature for 5 hours. The inorganic salts are removed by filtering the reaction mixture and the dimethylformamide is evaporated under reduced pressure. The residue is purified by crystallisation from methanol to give 83.2 g of a yellow beige powder.

Instantaneous melting point (Köfler) = 73° C.
Yield = 83.2%.

(b) p-(p-Chlorophenoxy)-aniline 91 g (0.364 mol) of the preceding product and 54.5 g (1.090 mols) of hydrazine hydrate are dissolved in 900 ml of methanol at about 50° C. This temperature is maintained and a sufficient amount of Raney nickel to decompose the hydrazine is added in small portions over the course of 5 hours, after which the mixture is heated to the reflux temperature for 1 hour. After having removed the catalyst by filtration in the presence of charcoal (CXA) and evaporated the solvent, purification by crystallisation from cyclohexane gives 60 g of light beige needles.

Instantaneous melting point (Köfler) = 101° C.
Yield = 75%.

(c) p-(p-Chlorophenoxy)-thiophenol 59.5 g (0.270 mol) of the preceding product are introduced, all at once, into a hot solution of 54 ml (0.675 mol) of 12.5 N hydrochloric acid and of 375 ml of water. The mixture is cooled and a solution of 22.6 g (0.298 mol) of sodium nitrite (taken to be 90% pure) in 100 ml of water is run in over the course of 45 minutes at between 0° and +5° C. The excess nitrous acid is destroyed with a pinch of urea (negative reactive on an iodine/starch paper). The reaction mixture is kept at about −5° C. and is run in portions, over the course of 1 hour 15 minutes, into a solution of 56 g (0.351 mol) of potassium ethyl-xanthate in 60 ml of water, kept at 40° C. Thereafter the oily suspension obtained is heated for 1 hour to 60° C. and the insoluble matter is extracted with diethyl ether to give, after evaporation of the solvent, 90.2 g of an orange-red oil.

This oil is treated for 4 hours with 38 g (0.675 mol) of potassium hydroxide pellets and 200 ml of water at the boil, then acidified to Congo Red with 6 N sulphuric acid and again treated at the boil for 2 hours in the presence of 5 g of zinc powder. The mixture is rendered alkaline with NaOH, the aqueous phase is washed with diethyl ether and acidification of the latter gives 45.85 g of a yellow powder.

Instantaneous melting point (Köfler)=55° C.
Yield=72.2%.

(d) Ethyl (±)-2-[4-(4-chlorophenoxy)-phenylthio]-propionate 8.4 g (0.0464 mol) of ethyl α-bromopropionate are run over the course of 10 minutes, at about 50° C., into a solution of 10 g (0.0422 mol) of the preceding product and 1 g (0.0422 mol) of sodium in 40 ml of anhydrous ethanol. The mixture is heated to the reflux temperature for 30 minutes, the inorganic salts are removed by filtration and the ethanol is driven off under reduced pressure. The residue is taken up in diethyl ether; the organic phase obtained is washed with water, dried over dry sodium sulphate and treated with charcoal (CXA). After evaporation of the solvent, 14.2 g of a limpid pale yellow oil which is insoluble in water are obtained.

Yield=about 100%.

(e) CRL 40,281

A solution of 14.2 g (0.0422 mol) of the preceding product and of 3.54 g (0.0635 mol) of potassium hydroxide pellets in 20 ml of water and 40 ml of ethanol is heated to the reflux temperature for 2 hours. The alcohol is evaporated under reduced pressure and the reaction mixture is diluted with water. The solution is acidified to Congo Red and the insoluble matter is extracted with diethyl ether. The organic phase obtained is in turn extracted with a potassium bicarbonate solution. After acidifying this aqueous phase with concentrated hydrochloric acid, 12.25 g of a pale yellow powder are isolated by extraction with diethyl ether. 12 g of this powder are purified by crystallisation and treatment with CXA charcoal in cyclohexane, to give 10 g of a white powder which is insoluble in water.

Instantaneous melting point (Köfler)=103° C.
Yield of stage e)=83.4%
Total yield=35.4%.

EXAMPLE 23

2-[4-(4-Chlorophenoxy)-phenoxy]ethanol

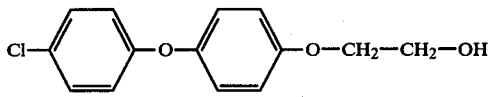

Code No. CRL 40,293

6.6 g (0.082 mol) of 2-chloro-ethanol are run over the course of 5 minutes into a hot solution of 15 g (0.068 mol) of p-(p-chlorophenoxy)-phenol and 2.75 g (0.068 mol) of sodium hydroxide pellets in 40 ml of anhydrous ethanol. The mixture is heated to the reflux temperature for 4 hours, the inorganic salts are removed by filtration and the ethanol is driven off under reduced pressure. After having taken up the reaction mixture in diethyl ether, washed the organic phase thus obtained with 2 N sodium hydroxide solution and with water, dried it and evaporated the solvent, 11 g of pasty crystals are obtained.

10.5 g of these crystals are purified by crystallisation from diisopropyl ether to give 6.7 g of shiny white flakes.

Instantaneous melting point (Köfler)=78° C.
Yield=39%.

EXAMPLE 24

4-(4-Chlorophenoxy)-phenoxy-isobutanol, alternative nomenclature:
2-[4-(4-chlorophenoxy)phenoxy]-2-methyl-1-propanol

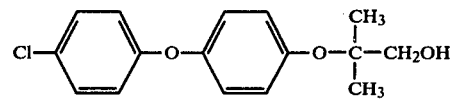

Code No. CRL 40,310

A solution of 12 g (0.0392 mol) of 4-(4-chlorophenoxy)-phenoxy-isobutyric acid (CRL 40,308) in 80 ml of anhydrous diethyl ether and 2 ml of tetrahydrofurane is run over the course of 30 minutes into a suspension of 3.35 g (0.0883 mol) of LiAlH$_4$ in 30 ml of anhydrous diethyl ether and the reflux is then maintained for 1 hour 30 minutes. The excess hydride is neutralised with ethyl acetate and the complex is hydrolysed with a diethyl hydrochloric acid solution. The organic phase is decanted and washed with water and dilute sodium hydroxide solution, and after drying and evaporation of the solvent gives 11.5 g of a thick yellow oil which is insoluble in water.

Yield about 100%.

EXAMPLE 25

4-(4-Chlorophenoxy)-phenoxy-isobutyl mesylate, alternative nomenclature:
2-[4-(4-chlorophenoxy)-phenoxy]-2-methylpropyl methanesulphonate

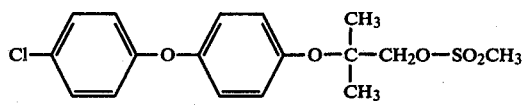

Code No. CRL 40,312

4.1 g (0.0356 mol) of methanesulphonyl chloride are run (over the course of 8 minutes) into a solution, kept at about 10° C., of 10.4 g (0.0356 mol) of 4-(4-chlorophenoxy)-phenoxy-isobutanol (CRL 40,310) in 17.5 ml of anhydrous pyridine, and the mixture is stirred for 1 hour at ambient temperature. The reaction mixture is poured onto ice and is acidified to Congo Red with concentrated hydrochloric acid. The insoluble matter is extracted with ethyl acetate and the organic phase thus obtained is washed with water, dried and evaporated to dryness under reduced pressure, to give 13.7 g of a yellow powder. The purification of this powder by crystallisation and treatment with charcoal (CXA) in diisopropyl ether gives 10.5 g of a white powder which is insoluble in water.

Instantaneous melting point (Köfler)=85° C.
Yield=78.3%.

EXAMPLE 26

(±)-2-[4-(4-Chlorophenoxy)-phenylthio]-1-propanol

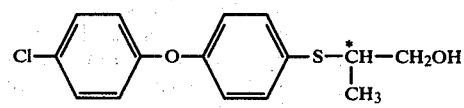

Code No. CRL 40,282

A solution of 9 g (0.291 mol) of (±)-2-[4-(4-chlorophenoxy)-phenylthiopropionic acid (CRL 40,281) in 75 ml of anhydrous diethyl ether and 2 ml of dried tetrahydrofurane is run over the course of 50 minutes into a suspension of 2.5 g (0.0656 mol) of LiAlH$_4$ in 20 ml of anhydrous diethyl ether. The mixture is heated to the reflux temperature for 1 hour, the excess hydride is destroyed with ethyl acetate and hydrolysis is carried out with a dilute hydrochloric acid solution. After washing the organic phase thus obtained with water and dilute sodium hydroxide solution, then drying it over dry sodium sulphate and evaporating the solvent, 8.6 g of a water-insoluble colourless oil having a yellow sheen is obtained.

Yield = about 100%.

EXAMPLE 27

(±)-2-[4-(4-Chlorophenoxy)-phenoxy]-1-propanol

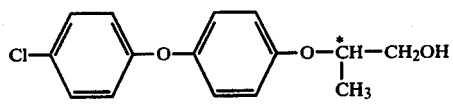

Code No. CRL 40,300

A solution of 22.5 g (0.077 mol) of (±)-2-[4-(4-chlorophenoxy)-phenoxy]-propionic acid (CRL 40299) in 150 ml of anhydrous diethyl ether is run over the course of 1 hour 30 minutes into a suspension of 6.6 g (0.173 mol) of LiAlH$_4$ in 50 ml of anhydrous diethyl ether. Thereafter the reflux is maintained for 1 hour 30 minutes, the excess hydride is neutralised with ethyl acetate and the complex is hydrolysed with dilute hydrochloric acid. The organic phase is decanted, washed with water and dilute sodium hydroxide solution and gives, after drying over dry sodium sulphate and evaporation of the solvent, 21.4 g of a crystalline white mass, which is insoluble in water.

Melting point <50° C.
Yield about 100%.

EXAMPLE 28

1-[4-(4-Chlorophenoxy)-phenoxy]-2-methyl-2-propanol

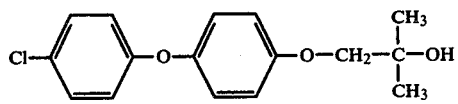

Code No. CRL 40,332

A solution of 8.15 g (0.075 mol) of 1-chloro-2-methyl-2-propanol in 20 ml of ethanol is run over the course of 25 minutes into a solution, kept at about 60° C., of 15 g (0.068 mol) of p-(p-chlorophenoxy)phenol and of 3 g (0.075 mol) of sodium hydroxide pellets in 20 ml of water and 20 ml of ethanol. The mixture is heated to the reflux temperature for 2 hours and the ethanol is driven off under reduced pressure. The residue is extracted with diethyl ether and after drying and evaporation of the solvent gives 7.3 g of a yellow oil. This oil is purified by crystallisation from a mixture of cyclohexane and petroleum ether (1:2 by volume) followed by washing with 2 N NaOH. 4 g of a white powder which is insoluble in water are obtained.

Instantaneous melting point (Köfler)=55° C.

Yield: 20.3%.

EXAMPLE 29

2-[4-(4-Chlorophenoxy)-phenoxy]-ethylamine hydrochloride

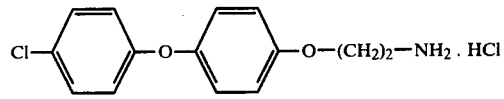

Code No. CRL 40,317

(a) 4-(4-Chlorophenoxy)-phenoxy-acetonitrile

A solution of 3.78 g (0.0500 mol) of chloroacetonitrile in 10 ml of anhydrous ethanol is run over the course of 20 minutes into a solution of 1.04 g (0.0453 mol) of sodium and 10 g (0.0453 mol) of p-(p-chlorophenoxy)-phenol in 50 ml of anhydrous ethanol and the mixture is then heated to the reflux temperature for 4 hours. It is evaporated to dryness under reduced pressure and the residue is dissolved in diethyl ether, which is washed with water and with dilute sodium hydroxide solution. After drying over dry sodium sulphate and evaporating the solvent from the organic phase, 12 g of an orange-coloured oil are obtained. Purification of this oil by distillation under reduced pressure gives 9.5 g of a limpid pale yellow oil which is insoluble in water.

Boiling point/0.4 mm Hg=165° C.
Yield=81%.

(b) CRL 40.317

A solution of 9 g (0.0347 mol) of the preceding nitrile in 50 ml of anhydrous diethyl ether is run over the course of 50 minutes into a suspension of 3.3 g (0.0868 mol) of LiAlH$_4$ in 40 ml of anhydrous diethyl ether. The mixture is heated to the reflux temperature for 1 hour, the excess hydride is neutralised with ethyl acetate and the complex is then hydrolysed with dilute sodium hydroxide solution. The organic phase is decanted, washed with water, dried over dry sodium sulphate and evaporated to give 7.5 g of a limpid pale yellow oil which crystallises.

4.5 g of this product in diethyl ether are treated with a solution of hydrogen chloride in ether. After purification of the precipitate obtained, by crystallisation and treatment with CXA charcoal, in a mixture of isopropanol and cyclohexane (1:1 by volume), 2 g of a beige powder which is soluble in water are obtained.

Instantaneous melting point (Köfler)=215° C.
Yield of stage (b)=21.4%

EXAMPLE 30

2-[4-(4-Chlorophenoxy)-phenoxy]-ethyl mesylate

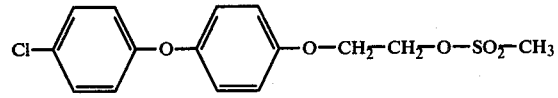

2.6 g (0.0227 mol) of methanesulphonyl chloride are run over the course of 5 minutes, at about +10° C., into a solution of 6 g (0.0227 mol) of 2-[4-(4-chlorophenoxy)-phenoxy]-1-ethanol (CRL 40,293) in 11 ml of pyridine and the mixture is then stirred for 1 hour at ambient temperature. Thereafter the reaction mixture is poured onto ice and acidified to Congo Red with concentrated hydrochloric acid. After extracting the insoluble matter with ethyl acetate, washing the organic phase obtained with water and drying it over dry sodium sulphate, evaporation of the solvent gives 7.8 g of a white powder.

Instantaneous melting point (Köfler)=68° C.
Yield about 100%.

EXAMPLE 31

N-Hydroxyethyl-2-[4-(4-chlorophenoxy)-phenoxy]-1-ethylamine hydrochloride

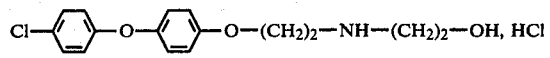

Code No. CRL 40 295

A mixture of 7.8 g (0.0227 mol) of the preceding product and of 13.8 g (0.2270 mol) of 2-aminoethanol is heated slowly to 170° C. The reaction mixture is allowed to return to ambient temperature and is taken up in water. After extracting the insoluble matter with diethyl ether, washing the extract with water, drying it and evaporating the solvent, 6.55 g of a white powder which is insoluble in water are obtained.

Instantaneous melting point (Köfler)=98° C.

6 g of this product, in ethyl acetate, are treated with a solution of hydrogen chloride in ether and the product is then purified by crystallisation from a mixture of ethanol and ethyl acetate (1:3 by volume), to give 5.6 g of a hydrochloride which is in the form of white flakes soluble in water to the extent of 200 g/l.

Instantaneous melting point (Köfler)=141° C.
Yield=77.5%

EXAMPLE 32

N,N-Diethyl-2-[4-(4-chlorophenoxy)-phenoxy]-ethylamine hydrochloride

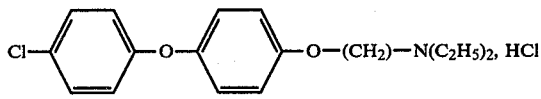

Code No. CRL 40 330

A solution of 13.2 g (0.075 mol) of 2-(N,N-diethylamino)-1-chloroethane hydrochloride in 30 ml of water is run over the course of 30 minutes into a solution, kept at about 60° C., of 15 g (0.068 mol) of p-(p-chlorophenoxy)-phenol and 6.3 g (0.157 mol) of sodium hydroxide pellets in 20 ml of water and 20 ml of ethanol. The mixture is heated to the reflux temperature for 1 hour and the ethanol is evaporated under reduced pressure. The aqueous phase is extracted with diethyl ether and the organic phase obtained is washed with water until neutral, dried over dry sodium sulphate and evaporated to dryness under reduced pressure. The oily residue is treated in a solution of hydrogen chloride in diethyl ether, to give 20 g of a white powder. Recrystallisation from ethyl acetate gives 18 g of CRL 40 330

Instantaneous melting point (Köfler)=119° C.
Yield 74.3%

EXAMPLE 33

N-Ethanol-2-[4-(4-chlorophenoxy)-phenoxy]-2-methyl-1-propylamine hydrochloride

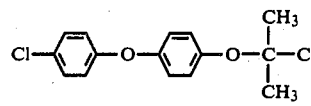

Code No. CRL 40 311

A solution of 7.8 g (0.0386 mol) of sodium bis-(2-methoxy-ethoxy)-aluminium hydride in 25 ml of benzene is run over the course of 45 minutes into a solution, at the reflux temperature, of 9 g (0.0257 mol) of N-ethanol-2-[4-(4-chlorophenoxy)-phenoxy]-2-methyl-1-propionamide (CRL 40 309), prepared as indicated in Example 38, in 40 ml of anhydrous benzene, and the reflux is maintained for a further 45 minutes. The complex is hydrolysed with dilute sodium hydroxide solution and the organic phase is decanted, washed with water and dried; evaporation of the solvent gives an orange-coloured oil.

This oil is treated with a solution of hydrogen chloride in diethyl ether, the precipitate obtained is isolated by filtration and the mother liquor is evaporated so as to recover the unreacted starting amide. Purification of the precipitate by a further conversion to the base and then to the salt, and by a crystallisation from a mixture of ethyl acetate and ethanol (1:1) in the presence of charcoal (CXA) gives 1.6 g of a white powder which is soluble in water.

Instantaneous melting point (Köfler)=133° C.

EXAMPLE 34

(±)-2-[4-(4-Chlorophenoxy)-phenoxyl]-propyl mesylate

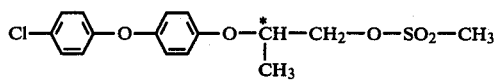

8.1 g (0.07 mol) of methanesulphonyl chloride are run, at about 10° C., into a solution of 19.5 g (0.07 mol) of (±)-2-[4-(4-chlorophenoxy)-phenoxy]-1-propanol (CRL 40 300) prepared as indicated in Example 27, in 35 ml of pyridine. The reaction mixture is stirred for 1 hour at ambient temperature and is poured onto ice. The insoluble matter is extracted with diethyl ether and the organic phase obtained is washed with dilute hydrochloric acid and dried, to give a white pasty residue after evaporation of the solvent. The solidification of this residue is petroleum ether gives 24 g of a white powder which is insoluble in water.

Melting point below 50° C.
Yield: 96.2%.

EXAMPLE 35

(±)-N-Hydroxyethyl-2-[4-(4-chlorophenoxy)-phenoxy]-1-propylamine hydrochloride

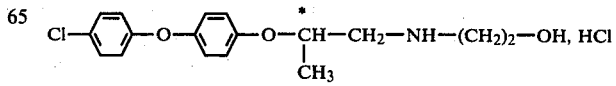

Code No. CRL 40 301

A mixture of 10 g (0.028 mol) of the mesylate of Example 34 and of 17 g (0.280 mol) of 2-aminoethanol is slowly heated to 170° C. The reaction mixture is allowed to return to ambient temperature and is taken up in water. After extracting the insoluble matter with diethyl ether, washing the organic phase with water and drying it over dry sodium sulphate, 8.7 g of a pale yellow oil are obtained after evaporation of the solvent. 8.4 g of this product, in ethyl acetate, are treated with a solution of hydrogen chloride in ether and the product is then purified by crystallisation from a mixture of ethyl acetate and anhydrous ethanol (7:2 by volume) to give 8.3 g of white flakes which are soluble in water to the extent of 200 g/l.

Instantaneous melting point (Köfler) = 145° C.
Yield = 86%

EXAMPLE 36

(±)-N-(β-Hydroxy-α,α-dimethylethyl)-2-[4-(4-chlorophenoxy)-phenoxy]-1-propylamine hydrochloride

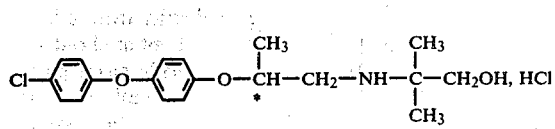

Code No. CRL 40 302

A mixture of 13 g (0.0365 mol) of the mesylate of Example 34 and of 32.5 g (0.365 mol) of 2-amino-2-methyl-1-propanol is heated slowly to 170° C. The reaction mixture is allowed to return to ambient temperature and is taken up in water. The insoluble matter is extracted with diethyl ether and the organic phase obtained is washed with water and dried over dry sodium sulphate to give, after evaporation of the solvent, 12.7 g of a limpid pale yellow oil. After treating 12 g of this oil in a solution of hydrogen chloride in diethyl ether, and purifying the product by crystallisation from ethyl acetate, 11.2 g of a white powder which is soluble in water to the extent of 200 g/l are obtained.

Instantaneous melting point (Köfler) = 125° C.
Yield = 84.2%

EXAMPLE 37

(±)-N-Hydroxyethyl-2-[4-(4-chlorophenoxy)-phenylthio]-1-propylamine

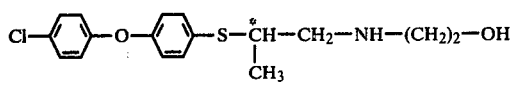

Code No. 40 283

(a)
2-Chloro-1-[4-(4-chlorophenoxy)-phenylthio]-propane 2.35 ml (0.0326 mol) of thionyl chloride are run, over the course of 7 minutes, into a solution of 8 g (0.0271 mol) of (±)-2-[4-(4-chlorphenoxy)-phenylthio]-1-propanol (CRL 40 282) prepared as indicated in Example 26 and of 0.5 ml of pyridine in 30 ml of anhydrous benzene. The reaction mixture is heated to the reflux temperature for 1 hour and is washed with water and with a potassium bicarbonate solution. After drying over dry sodium sulphate and evaporating the solvent, 8.05 g of a limpid pale yellow oil which is insoluble in water are obtained.

Yield 95%.

(b) CRL 40 283

A mixture of 7.95 g (0.0254 mol) of the preceding product and of 7.75 g (0.1270 mol) of 2-aminoethanol is heated gradually to 170° C. over the course of 1 hour. The reaction mixture is taken up with diethyl ether, which is washed with water. The aqueous phase is extracted with a dilute hydrochloric acid solution; the insoluble oil between the two phases is isolated, taken up in water and extracted with diethyl ether in the presence of potassium carbonate. After drying the organic phase over dry sodium sulphate, treating it with CXA charcoal, and evaporating the solvent, 7.8 g of a yellow oil are obtained. 6 g of this oil are purified by a further base/salt conversion to give 5.75 g of a pale yellow oil which is soluble in an aqueous hydrochloric acid solution at between pH 3 and pH 7.

Yield of stage (b) = 87.2%
Total yield = 83%

EXAMPLE 38

N-Hydroxyethyl-2-[4-(4-chlorophenoxy)-phenoxy]-2-methylpropionamide

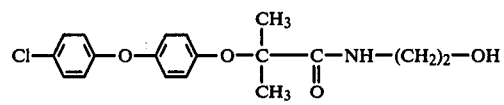

Code No. 40 309

(a) 2-[4-(4-Chlorophenoxy)-phenoxy]-methyl-propionyl chloride

A mixture of 12 g (0.0392 mol) of 4-(4-chlorophenoxy)-phenoxy-isobutyric acid (CRL 40 308) prepared as described in Example 21, and of 14.15 ml (0.1960 mol) of thionyl chloride is heated to the reflux temperature for 50 minutes. The reaction mixture is taken up in benzene, the solution is filtered in the presence of CXA charcoal, and after having evaporated the solvent under reduced pressure 12.5 g of a brown-red oil are obtained.

Yield = 95.5%.

(b) CRL 40 309

A solution of 12 g (0.0369 mol) of the preceding product in 40 ml of anhydrous benzene is run (over the course of 15 minutes), at between 20° and 36° C., into a suspension of 11.3 g (0.1850 mol) of ethanolamine in 30 ml of anhydrous benzene. The reaction mixture is heated to the reflux temperature for 1 hour and is then washed successively with water, dilute sodium hydroxide solution and a dilute hydrochloric acid solution. After drying over dry sodium sulphate, filtering, and evaporating the solvent from the organic phase, an orange-red crystalline mass is obtained. CRL 40 309 is purified by crystallisation, and treatment with CXA charcoal, in diisopropyl ether, to give 10.25 g of a slightly yellow powder which is insoluble in water.

Instantaneous melting point (Köfler) = 77° C.
Yield of stage (b) = 79.5%
Total yield = 76%.

EXAMPLE 39

N-(2-Diethylaminoethyl)-4-(4-chlorophenoxy)-phenoxy-acetamide hydrochloride

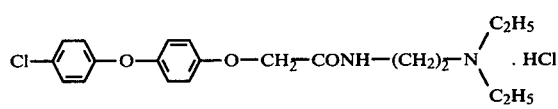

Code No. CRL 40 334

(a) 4-(4-Chlorophenoxy)-phenoxy-acetyl chloride

A mixture of 8.3 g (0.0298 mol) of 4-(4-chlorophenoxy)-phenoxy-acetic acid (CRL 40 333) prepared as indicated in Example 19 and of 10.8 ml (0.1500 mol) of thionyl chloride is heated to the reflux temperature for 30 minutes. After having taken up the reaction mixture in benzene and evaporated the solution to dryness under reduced pressure, 8.7 g of a beige powder are obtained.
Instantaneous melting point (Köfler)=64° C.
Yield=98.3%

(b) CRL 40 334

A solution of 8.5 g (0.0286 mol) of the preceding product in 20 ml of anhydrous benzene is run over the course of 15 minutes, at between 20° C. and 40° C., into a solution of 16.6 g (0.1430 mol) of N,N-diethyl-ethylenediamine in 30 ml of anhydrous benzene. The reaction mixture is heated to the reflux temperature for 30 minutes and is then washed with water. After drying, and evaporating the solvent from the organic phase, 10.75 g of an orange-coloured oil are obtained.

9.5 g of this oil, in diisopropyl ether, are treated with a solution of hydrogen chloride in ether and the precipitate obtained is purified by crystallisation from ethyl acetate to give 9.8 g of a slightly beige powder which is soluble in water.
Instantaneous melting point (Köfler)=120° C.
Yield of stage b=94.5%
Total yield=93%

EXAMPLE 40

4-(4-Chlorophenoxy)-phenoxy-acetamidoxime hydrochloride

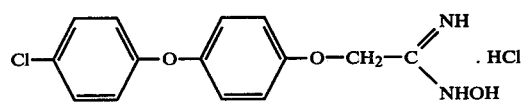

Code No. CRL 40 337

A suspension of 5.37 g (0.0772 mol) of hydroxylamine hydrochloride and of 7.72 g (0.0772 mol) of potassium bicarbonate in 8 ml of water is added, all at once, to a suspension of 10 g (0.0385 mol) of 4-(4-chlorophenoxy)-phenoxy-acetonitrile prepared as indicated in Example 29a), in 24 ml of n-butanol. The mixture is heated to the reflux temperature for 1 hour, the butanol is driven off, the residue is taken up in water and the insoluble matter is extracted with diethyl ether. The organic phase is washed with water, dried over dry sodium sulphate and evaporated, and the residue obtained is purified by washing with hot diisopropyl ether to give 10 g of brilliant white needles.
Instantaneous melting point (Köfler)=99° C.

After treating 9.5 g of this product in a solution of hydrogen chloride in diethyl ether and purifying the product by crystallisation from isopropanol, 10.15 g of a white powder which is partially soluble in water are obtained.
Instantaneous melting point (Köfler)=148° C.
Yield=85%

EXAMPLE 41

4-(4-Chlorophenoxy)-phenoxy-acetamidine hydrochloride

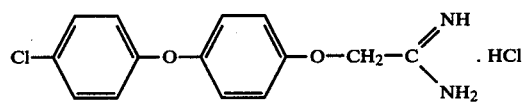

Code No. CRL 40 338

(a) Ethyl 4-(4-chlorophenoxy)-phenoxy-acetimidate hydrochloride

A solution of 15 g (0.0578 mol) of 4-(4-chlorophenoxy)-phenoxy-acetonitrile prepared as indicated in Example 29a) and of 3.7 ml (0.0637 mol) of anhydrous ethanol in 75 ml of anhydrous diethyl ether is kept at about −5° C. and a stream of dry hydrogen chloride gas is passed into it for 2 hours. Thereafter the reaction mixture is left for 4 hours at about 2° C. and 19.25 g of a white powder are isolated by filtration.
Instantaneous melting point (Köfler)=148° C.
Yield=97.5%

(b) CRL 40 338

A stream of NH3 is passed over the course of 1 hour at about 10° C. into a solution of 10 g (0.0292 mol) of the preceding product in 100 ml of anhydrous ethanol. The reaction mixture is stirred for 4 hours at ambient temperature and is then evaporated to dryness under reduced pressure. After purifying the residue by washing it with diethyl ether, 8.55 g of a white powder are obtained. 7.55 g of this powder are again purified by a crystallisation and a treatment with CXA charcoal in isopropanol, to give 6.05 g of a white product which is soluble in water.
Instantaneous melting point (Köfler)=166° C.
Yield of stage (b)=75.5%

EXAMPLE 42

2-[4-(4-Chlorophenoxy)-phenoxy]-methyl-2-imidazoline hydrochloride

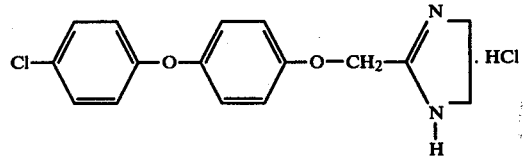

Code No. CRL 40 322

A solution of 6 g (0.0175 mol) of the product of Example (41a) and of 1.25 ml (0.0184 mol) of ethylenediamine in 40 ml of anhydrous ethanol is heated to the reflux temperature for 2 hours 30 minutes. The ethanol is driven off under reduced pressure, the residue is taken up in dilute sodium hydroxide solution and the insoluble matter is extracted with diethyl ether. The product obtained after evaporation of the solvent is purified by washing it with diisopropyl ether, to give 4 g of a white powder which is insoluble in water.

Instantaneous melting point (Köfler)=117° C.

After treating 3.8 g of this powder, in ethyl acetate, with a solution of hydrogen chloride in ether, 3.8 g of a white powder which is soluble in hot water are obtained.

Instantaneous melting point (Köfler)=166° C. Yield=80.5%.

The examples which follow illustrate the production of (a) addition salts with acids (compare Examples 43–45 and 47–48) and (b) an ester (compare Example 46) from an acid of the formula I (R=COOH) and from a free base belonging to the group of bis-[(N-hydroxyalkyl)-amino-alkylthio]-alkanes of the formula:

Bo-NRo-Ao-SO$_x$-(CH$_2$)$_n$-SO$_x$-Ao-NRo-Bo

More precisely, the acids which were used are:
for Examples 43 and 46, CRL 40 201, which has been described in Example 17,
for Example 44, CRL 40 239 which has been described in Example 3,
for Example 45, CRL 40 248 which has been described in Example 6,
for Example 47 CRL 40 202 which has been been described in Example 18, and
for Example 48, CRL 40 246 which has been described in Example 5.

The free base used in Examples 43–48 is 6,17-dithia-3,20-diaza-1,22-docosanediol, which in the form of the dihydrochloride has been given Code No. LL 1,770.

EXAMPLE 43

6,17-Dithia-3,20-diaza-1,22-docosanediol di-p-(p-chlorophenylthio)-phenoxy-isobutyrate

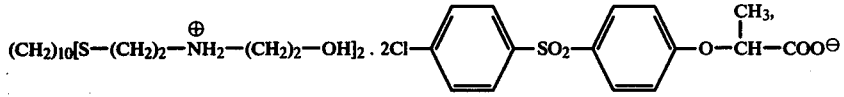

Code No. CRL 40 240

A hot solution of 6.45 g (0.02 mol) of p-(p-chlorophenylthio)-phenoxy-isobutyric acid in 25 ml of anhydrous ethanol is run into a hot solution of 3.8 g (0.01 mol) of 6,17-dithia-3,20-diaza-1,22-docosanediol (free base of LL 1,770) in 25 ml of anhydrous ethanol. The mixture is stirred for 2 hours at ambient temperature and the solvent is then evaporated under reduced pressure. After having washed the residue with acetonitrile, 8.4 g of a slightly beige powder which is insoluble in water but soluble in alcohol are obtained. Instantaneous melting point (Köfler)=75° C. Yield=82%.

EXAMPLE 44

6,17-Dithia-3,20-diaza-1,22-docosanediol di-p-(p-chlorophenylsulphonyl)-phenoxy-isobutyrate

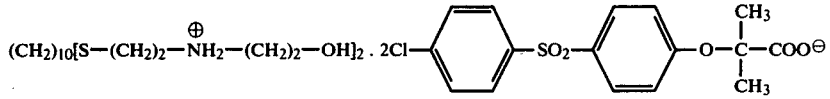

Code No. CRL 40241

A hot solution of 6.6 g (0.0186 mol) of p-(p-chlorophenylsulphonyl)-phenoxy-isobutyric acid in 25 ml of anhydrous ethanol is run into a hot solution of 3.54 g (0.0093 mol) of 6,17-dithia-3,20-diaza-1,22-docosanediol in 25 ml of anhydrous ethanol. The mixture is stirred for 2 hours at ambient temperature and the solvent is then evaporated under reduced pressure. After having washed the residue with acetonitrile, 9.9 g of a slightly pink powder which is insoluble in water and soluble in hot alcohol are obtained. Instantaneous melting point (Köfler)=137° C. Yield 98%.

EXAMPLE 45

6,17-Dithia-3,20-diaza-1,22-docosanediol di-(±)-2-[p-(p-chlorophenylsulphonyl)-phenoxy]-propionate

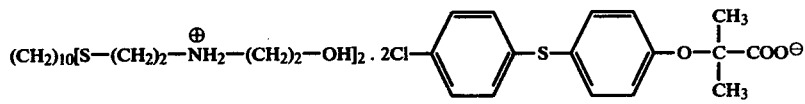

Code No. CRL 40249

A hot solution of 5.10 g (0.0150 mol) of (±)-2-[p-(p-chlorophenylsulphonyl)-phenoxy]-propionic acid in 20 ml of anhydrous ethanol is run into a hot solution of 2.84 g (0.0075 mol) of 6,17-dithia-3,20-diaza-1,22-docosanediol (free base of LL 1,770) in 20 ml of anhydrous ethanol. After having left the reactants in contact for 15 minutes the solvent is evaporated under reduced pressure. The crystalline residue is then washed with acetonitrile to give 7.8 g of a white powder which is insoluble in water and in alcohol. Instantaneous melting point (Köfler)=149°–150° C. Yield: 98.3%.

EXAMPLE 46

3,20-di[p-(p-chlorophenylthio)phenoxy-isobutyryl]-6,17-dithia-3,20-diaza-1,22-docosanediol

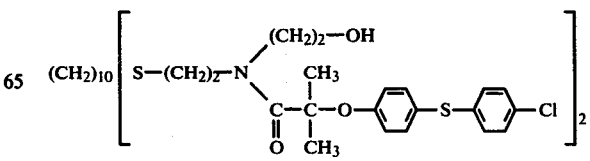

Code No. CRL 40 254

(a) p-(p-Chlorophenylthio)-phenoxy-isobutyryl chloride

A mixture of 15 g (0.0465 mol) of p-(chlorophenylthio)phenoxy-isobutyric acid and of 16.75 ml (0.2320 mol) of thionyl chloride is heated to the reflux temperature for 10 minutes. After having taken up the reaction mixture in benzene, filtered the solution in the presence of charcoal and evaporated the solvent, 16 g of an orange-coloured oil are obtained. Yield: 100%.

(b) CRL 40 254

A solution of 17 g (0.050 mol) of the acid chloride obtained as above, in 50 ml of chloroform, is run over the course of 50 minutes, at 0° C., into a suspension of 9.5 g (0.025 mol) of 6,17-dithia-3,20-diaza-1,22-docosanediol (free base of LL 1,770) and of 5 g (0.050 mol) of triethylamine in 75 ml of chloroform. After having stirred the reaction mixture overnight at ambient temperature, it is washed successively with water, a dilute hydrochloric acid solution and a potassium bicarbonate solution, and the solvent is then evaporated under reduced pressure, to give 23 g of a thick orange-coloured oil. After purification of 15 g of this oil by chromatography on a silica column, 7.7 g of a limpid orange-coloured oil which is insoluble in water are obtained.

Total yield = 48%.

EXAMPLE 47

6,17-Dithia-3,20-diaza-1,22-docosanediol di-[4-(4-chlorosulphinyl)-phenoxy-isobutyrate]

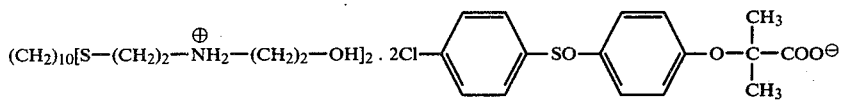

Code No. CRL 40 242

A hot solution of 6.77 g (0.02 mol) of CRL 40 202 in 25 ml of ethanol is run into a hot solution of 3.8 g (0.01 mol) of 6,17-dithia-3,20-diaza-1,22-docosanediol in 25 ml of ethanol. The mixture is stirred for 30 minutes at ambient temperature and the solvent is then evaporated under reduced pressure. After having solidified the residue in diisopropyl ether, 10.4 g of a white powder which is insoluble in water and soluble in alcohol are obtained.

Instantaneous melting point (Köfler) = about 85° C.
Yield = 98.5%

EXAMPLE 48

6,17-Dithia-3,20-diaza-1,22-docosanediol di-(±)-[2-(4-chlorophenylthio)phenoxy-propionate]

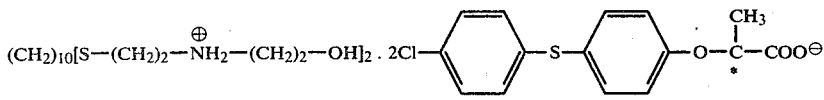

Code No. CRL 40 247

A hot solution of 4.62 g (0.015 mol) of CRL 40 246 in 20 ml of anhydrous ethanol is run into a hot solution of 2.84 g (0.0075 mol) of 6,17-dithia-3,20-diaza-1,22-docosanediol in 20 ml of anhydrous ethanol. After having left the reactants in contact for 15 minutes, the solvent is evaporated under reduced pressure. The residue is then solidified in acetonitrile to give 7.2 g of a white powder which is insoluble in water and soluble in alcohol.

Instantaneous melting point (Köfler) = about 70° C.
Yield = 96.5%

The examples which follow illustrate the preparation of dithio-acids (A=B=S).

EXAMPLE 49

(±)-2-[p-(p-Chlorophenylthio)-phenylthio]-propionic acid

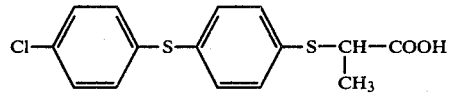

Code No.: CRL 40,351

(a) Preparation of copper p-chlorophenylthiolate

A suspension of 115 g (0.760 mol) of p-chlorothiophenol, taken to be 95% strength, and of 35.8 g (0.250 mol) of cuprous oxide in 600 ml of 95% strength ethanol is heated under reflux for 20 hours. After having filtered the precipitate and washed it copiously with alcohol, 103.7 g of a yellow powder are obtained.
Yield = 100%.

(b) Preparation of ethyl (±)-2-(p-bromophenylthio)-propionate

A solution of 30 g (0.165 mol) of ethyl 2-bromopropionate in 30 ml of anhydrous ethanol is run over the course of 30 minutes into a solution of 29 g (0.150 mol) of p-bromothiophenol, taken as 98% strength, and of 6 g (0.150 mol) of sodium hydroxide pellets in 100 ml of anhydrous ethanol, and the mixture is then stirred for 1 hour at ambient temperature. The inorganic salts formed are removed by filtration and the alcohol is evaporated. The residue is taken up in diethyl ether and the organic phase obtained is washed successively with N sodium hydroxide solution and with water. After drying, and evaporating the solvent, 44.6 g of a limpid pale yellow oil are obtained. The purification of this oil by distillation under reduced pressure gives 37.1 g of a limpid colourless oil.

Boiling point/4 mm Hg = 143°–145° C.
Yield = 85.3%.

(c) Preparation of ethyl (±)-2-[p-(p-chlorophenylthio)-phenylthio]-propionate A suspension of 29.8 g (0.144 mol) of copper p-chlorophenylthiolate obtained according to (a) and of 37 g (0.128 mol) of the ester obtained in (b), in 96 ml of quinoline and 26.5 ml of pyridine, is heated for 3 hours at about 170° C. The reaction mixture is then poured onto ice and is acidified with concentrated hydrochloric acid, using Congo Red as the indicator. After extracting the insoluble matter with diethyl ether, drying and evaporating the solvent, 48 g of a brown oil are obtained.

Yield = 100%

(d) CRL 40,351

A solution of 48 g (about 0.128 mol) of the above product and of 12 g (0.216 mol) of KOH pellets in 150 ml of ethanol and 50 ml of water is heated under reflux for 1 hour 30 minutes. The alcohol is evaporated and the reaction mixture is diluted with water and acidified with concentrated hydrochloric acid. The precipitate is extracted with diethyl ether and the organic phase obtained is in its turn extracted with a solution of potassium bicarbonate. Acidification of the aqueous phase with hydrochloric acid liberates 40 g of an orange oil which is extracted with diethyl ether.

This oil is purified by two successive crystallisations from cyclohexane and one crystallisation from a 50:50 v/v mixture of heptane and benzene, to give 25 g of a white, water-insoluble powder.

Instantaneous melting point (Köfler) = 71° C.
Yield from stage (d) = 61.3%
Overall yield = 52.3%

EXAMPLE 50

2-[p-(p-Chlorophenylthio)-phenylthio]-2-methylpropionic acid

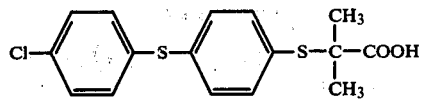

Code No.: CRL 40,356

Following the procedure indicated in Example 49b 47 g of a limpid pale yellow oil are prepared from 29 g (0.150 mol) of p-bromothiophenol and 32.2 g (0.165 mol) of ethyl 2-bromo-2-methylpropionate; subsequent purification of this oil (by distillation under reduced pressure) gives 40.8 g of ethyl 2-(p-bromophenylthio)-2-methylpropionate.

Boiling point/2-3 mm Hg = 142°-143° C.
Yield = 90%.

Reaction of copper p-chlorophenylthiolate with ethyl 2-(p-bromophenylthio)-2-methylpropionate in accordance with the procedure given in Example 49(c), gives ethyl 2-[p-(p-chlorophenylthio)-phenylthio]-2-methylpropionate (which is in the form of an orange oil).

This ester is hydrolysed in accordance with the procedure given in Example 49(d); subsequent purification (treatment with charcoal and recrystallisation from diisopropyl ether) gives CRL 40,356.

Instantaneous melting point (Köfler) = 140° C.

EXAMPLE 51 p-(p-Chlorophenylthio)-phenylthioacetic acid

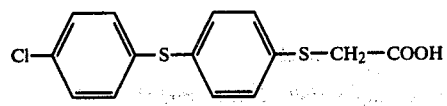

Code No.: CRL 40,363

Following the procedure indicated in Example 49(b), ethyl p-bromophenylthio-acetate (boiling point/7 mm Hg = 163°-165° C.) is prepared and this ester is reacted with copper p-chlorophenylthiolate in accordance with Example 49(c) to give ethyl p-(p-chlorophenylthio)-phenylthio-acetate which, by hydrolysis followed by purification (charcoal, and recrystallisation from diisopropyl ether) gives CRL 40,363.

Instantaneous melting point (Köfler) = 110° C.

The examples which follow are concerned with the preparation of diesters from bis-[(S-hydroxyalkyl)thio]-alkanes.

EXAMPLE 52

3,14-Dithia-1,16-hexadecyl di-[p-(p-chlorophenoxy)-phenylthio-acetate]

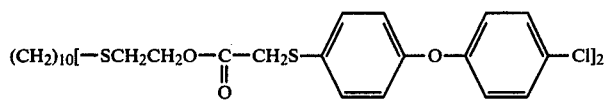

Code No.: CRL 40,284

(a) p-(p-Chlorophenoxy)-phenylthio-acetyl chloride

A mixture of 17.5 g (0.0595 mol) of p-(p-chlorophenoxy)-phenylthio-acetic acid (Code No. CRL 40,271) and of 21.6 ml (0.3000 mol) of thionyl chloride is heated under reflux for 30 minutes. After having taken up the reaction mixture in benzene, filtered the solution in the presence of charcoal and evaporated the solvent, 18.5 g of a limpid orange-yellow oil are obtained.

Yield = 99.5%.

(b) CRL 40,284

A solution of 9.5 g (0.0303 mol) of the above product in 20 ml of benzene is run, over the course of 40 minutes, into a hot solution of 4 g (0.0136 mol) of 3,14-dithia-1,16-hexadecanediol (Code No. LL 1,558) in 25 ml of benzene. The mixture is heated under reflux for 2 hours, the reactants are left in contact at ambient temperature for 48 hours, and the mixture is then evaporated to dryness under reduced pressure. After having dissolved the residue in chloroform, washed the solution with water and potassium carbonate and evaporated the solvent, a crystalline yellowish product is obtained. This product is purified by washing with diethyl ether to give 9.7 g of a white, water-insoluble powder.

Instantaneous melting point (Köfler) = 70°-71° C.
Yield of stage (b) = 84.4%.
Overall yield = 84%.

EXAMPLES 53 to 74

On proceeding as indicated in Example 52, starting from the following acids: 2-[p-(p-chlorophenoxy)-phenoxy]-2-methylpropionic acid (Code No.: CRL 40,308), (±)-2-[p-(p-chlorophenoxy)-phenoxy]-propionic acid (Code No.: CRL 40,299), p-(p-chlorophenoxy)-phenoxy-acetic acid (Code No.: CRL 40,333), 2-[p-(p-chlorophenylthio)-phenoxy]-2-methylpropionic acid (Code No.: CRL 40,201), p-(p-chlorophenylthio)-phenoxy-acetic acid (Code No.: CRL 40,386), (±)-2-[p-(p-chlorophenylthio)-phenoxy]-propionic acid (Code No.: CRL 40,246), p-(p-chlorophenylthio)-phenylthio-acetic acid (Code No.: CRL 40,363), (±)-2-[p-(p-chlorophenylthio)-phenylthio]-propionic acid (Code No.: CRL 40,351), 2-[p-(p-chlorophenylthio)-phenylthio]-2-methylpropionic acid (Code No.: CRL 40,356), p-(p-chlorophenoxy)-phenylthio-acetic acid (already used above in the synthesis of the product of Example 52), (±)-2-[p-(p-chlorophenoxy)-phenylthio]-propionic acid (Code No.: CRL 40,281) and 2-[p-(p-chlorophenoxy)-phenylthio]-2-methylpropionic acid (Code No.: CRL 40,275), which are reacted, in the form of the acid chlorides, with 3,14-dithia-1,16-hexadecanediol (Code No.: LL 1,558) or (±)-2,15-dimethyl-3,14-dithia-1,16-hexadecanediol (Code No.: CRL 40,122), the esters (shown in Table II) are obtained, namely:

EXAMPLE 53

3,14-Dithia-1,16-hexadecyl di-{2-[p-(p-chlorophenoxy)-phenoxy]-2-methylpropionate} (Code No.: CRL 40,368);

EXAMPLE 54

(±)-2,15-Dimethyl-3,14-dithia-1,16-hexadecyl di-{2-[p-(p-chlorophenoxy)-phenoxy]-2-methylpropionate} (Code No.: CRL 40,374);

EXAMPLE 55

3,14-Dithia-1,16-hexadecyl di-(±)-{2-[p-(p-chlorophenoxy)-phenoxy]-propionate} (Code No.: 40,377);

EXAMPLE 56

(±)-2,15-Dimethyl-3,14-dithia-1,16-hexadecyl di-(±)-{2-[p-(p-chlorophenoxy)-phenoxy]-propionate} (Code No.: CRL 40,378);

EXAMPLE 57

3,14-Dithia-1,16-hexadecyl di-[p-(p-chlorophenoxy)-phenoxy-acetate] (Code No.: CRL 40,379);

EXAMPLE 58

(±)-2,15-Dimethyl-3,14-dithia-1,16-hexadecyl di-[p-(p-chlorophenoxy)-phenoxy-acetate] (Code No.: CRL 40,380);

EXAMPLE 59

(±)-2,15-Dimethyl-3,14-dithia-1,16-hexadecyl di-{2-[p-(p-chlorophenylthio)-phenoxy]-2-methylpropionate} (Code No.: CRL 40,387);

EXAMPLE 60

3,14-Dithia-1,16-hexadecyl di-[p-(p-chlorophenylthio)-phenoxy-acetate] (Code No.: CRL 40,388);

EXAMPLE 61

(±)-2,15-Dimethyl-3,14-dithia-1,16-hexadecyl di-[p-(p-chlorophenylthio)-phenoxy-acetate] (Code No.: CRL 40,389);

EXAMPLE 62

3,14-Dithia-1,16-hexadecyl di-(±)-{2-[p-(p-chlorophenylthio)-phenoxy]-propionate} (Code No.: CRL 40,390)

EXAMPLE 63

(±)-2,15-Dimethyl-3,14-dithia-1,16-hexadecyl di-(±)-{2-[p-(p-chlorophenylthio)-phenoxy]-propionate} (Code No.: CRL 40,391);

EXAMPLE 64

3,14-Dithia-1,16-hexadecyl di-[p-(p-chlorophenylthio)-phenylthio-acetate] (Code No.: CRL 40,394);

EXAMPLE 65

(±)-2,15-Dimethyl-3,14-dithia-1,16-hexadecyl di-[p-(p-chlorophenylthio)-phenylthio-acetate] (Code No.: CRL 40,395);

EXAMPLE 66

3,14-Dithia-1,16-hexadecyl di-(±)-{2-[p-(p-chlorophenylthio)-phenylthio]-propionate} (Code No.: CRL 40,398);

EXAMPLE 67

(±)-2,15-Dimethyl-3,14-dithia-1,16-hexadecyl di-(±)-{2-[p-(p-chlorophenylthio)-phenylthio]-propionate} (Code No.: CRL 40,399);

EXAMPLE 68

3,14-Dithia-1,16-hexadecyl di-{2-[p-(p-chlorophenylthio)-phenylthio]-2-methylpropionate} (Code No.: CRL 40,402);

EXAMPLE 69

(±)-2,15-Dimethyl-3,14-dithia-1,16-hexadecyl di-{2-[p-(p-chlorophenylthio)-phenylthio]-2-methylpropionate} (Code No.: CRL 40,403);

EXAMPLE 70

(±)-2,15-Dimethyl-3,14-dithia-1,16-hexadecyl di-[p-(p-chlorophenoxy)-phenylthio-acetate] (Code No.: CRL 40,405);

EXAMPLE 71

3,14-Dithia-1,16-hexadecyl di-(±)-{2-[p-(p-chlorophenoxy)-phenylthio]-propionate} (Code No.: CRL 40,408);

EXAMPLE 72

(±)-2,15-Dimethyl-3,14-dithia-1,16-hexadecyl di-(±)-{2-[p-(p-chlorophenoxy)-phenylthio]-propionate} (Code No.: CRL 40,409);

EXAMPLE 73

3,14-Dithia-1,16-hexadecyl di-{2-[p-(p-chlorophenoxy)-phenylthio]-2-methylpropionate} (Code No.: CRL 40,413);

EXAMPLE 74

(±)-2,15-Dimethyl-3,14-dithia-1,16-hexadecyl di-{2-[p-(p-chlorophenoxy)-phenylthio]-2-methylpropionate} (Code No.: CRL 40,414).

EXAMPLE 75

3,14-Dithia-1,16-hexadecyl di-[4-(4-chlorophenylthio)-phenoxyisobutyrate]

$$\left[ (CH_2)_{10} \quad S-(CH_2)_2-O-\underset{\underset{O}{\|}}{C}-\underset{\underset{CH_3}{|}}{\overset{\overset{CH_3}{|}}{C}}-O-\underset{}{\bigcirc}-S-\underset{}{\bigcirc}-Cl \right]_2$$

Code No. CRL 40,253

(a) p-(p-Chlorophenylthio)-phenoxy-isobutyroyl chloride

A mixture of 15 g (0.0465 mol) of p-(p-chlorophenylthio)-phenoxy-isobutyric acid (CRL 40,201) and of 16.75 ml (0.232 mol) of thionyl chloride is heated to the reflux temperature for 10 minutes. After having taken up the reaction mixture in benzene, filtered the solution in the presence of carbon black and evaporated the solvent, 16 g of an orange-coloured oil are obtained.

Yield = about 100%.

(b) CRL 40,253

A solution of 13 g (0.038 mol) of the preceding acid chloride in 25 ml of benzene is run over the course of 15 minutes into a suspension of 5 g (0.017 mol) of bis-1,10-(2-hydroxy-ethylthio)-decane in 20 ml of benzene and 3 g (0.038 mol) of pyridine at between 20° and 55° C. The reactants are left in contact overnight at ambient temperature and the reaction mixture is then washed with dilute hydrochloric acid. After drying over dry sodium sulphate and evaporating the solvent, 17.5 g of an orange-coloured oil are obtained. This oil is dissolved in diethyl ether and purified by 2 successive washes with potassium carbonate followed by dilute sodium hydroxide solution, giving 15.55 g of an orange-coloured oil which is insoluble in water.

Yield = 94%.

The results of the pharmacological tests which were undertaken both in respect to the hypo-lipidaemic properties and hypo-cholesterolaemic properties, on the one hand, and of the anti-aggregation properties, on the other, have been summarised below.

The hypo-lipidaemic action and hypo-cholesterolaemic action have been demonstrated by studying various batches of Wistar rats:

A. A batch of rats receiving a normal diet (percentage inhibition = 100%);
B. a batch of rats receiving a hyper-lipid diet (percentage inhibition = 0%);
C. a batch of rats receiving the hyper-lipid diet B with a daily dose, of 0.1 g/kg, of a reference product having a lipidaemia-normalising action, namely Lipavlon [ethyl 2-(p-chlorophenoxy)-2-methyl-propionate];
D. a batch of rats receiving the hyper-lipid diet B with a daily dose, of 0.1 g/kg, of another product having a lipidaemia-normalising action, namely LL 1558 [1,10-bis-(2-hydroxyethyl-thio)-decane]; and
E. a batch of rats receiving the hyper-lipid diet B with a daily dose of 10 mg/kg and 25 mg/kg, where necessary, higher doses.

The anti-aggregation action has been demonstrated by studying the parameters which characterise the curve for the aggregation of platelets induced;
(a) by collagen: the inhibition of aggregation (which corresponds to the % transmission), the latency period and the speed; and
(b) by ADP: the inhibition of aggregation (that is to say the % transmission).

In Table III which follows have been shown the results relating to CRL 40,201 (the product of Example 17) and CRL 40,202 (the product of Example 18) in respect of the hypo-lipidaemic action and hypo-cholesterolaemic action.

Table III shows that CRL 40,201 and CRL 40,202 are very active hypo-lipidaemic and hypo-cholesterolaemic agents because at a dose of 0.025 g/kg they each have an activity comparable to the two reference products administered at a dose of 0.1 g/kg.

In Table IV which follows have been shown the results relating to the anti-aggregation action of some products on the blood of male Wistar rats, the aggregating agents used being collagen/acetic acid diluted 1/10, and ADP at 1 μM.

TABLE III

| Diet and product administered orally | Total lipids | | Total cholesterol | |
|---|---|---|---|---|
| | g/l | % inhibition | g/l | % inhibition |
| Normal diet | 3.05 | 100 | 0.81 | 100 |
| Hyper-lipid diet | 11.6 | 0 | 4.62 | 0 |
| Hyper-lipid diet + daily dose of 0.1 g/kg of Lipavlon | 10.4 | 14 | 4.18 | 11 |
| Hyper-lipid diet + daily dose of 0.1 g/kg of LL 1558 | 7 | 54 | 2.22 | 63 |
| Hyper-lipid diet + daily dose of 0.025 g/kg of CRL 40,201 | 7.7 | 45 | 2.8 | 48 |
| Hyper-lipid diet + daily dose of 0.010 g/kg of CRL 40,201 | 9 | 30 | 3.28 | 35 |
| Hyper-lipid diet + daily dose of 0.025 g/kg of CRL 40,202 | 7.05 | 53 | 2.38 | 59 |
| Hyper-lipid diet + daily dose of 0.010 g/kg of CRL 40,202 | 9.28 | 27 | 3.64 | 26 |

TABLE IV

| Example | Code No. | Oral dose, mg/kg | Duration of the treatment | Change in aggregation | | | ADP transmission |
|---|---|---|---|---|---|---|---|
| | | | | Collagen | | | |
| | | | | Latency period | Speed | Transmission | |
| 2 | CRL 40,238 | 100 | 4 days | +18% | −52% | −47% | −46% |
| 7 | CRL 40,251 | 200 | 4 days | +23% | −21% | − 5% | − 4% |
| 10 | CRL 40,271 | 100 | 4 days | +15% | −60% | −25% | −28% |
| 11 | CRL 40,272 | 100 | 4 days | +16% | − 7% | 0% | −20% |
| 12 | CRL 40,274 | 100 | 4 days | + 5% | 0% | − 3% | −20% |
| 14 | CRL 40,276 | 100 | 4 days | +25% | −13% | −31% | −20% |

The results of Table IV show that the products studied are anti-aggregation agents, the most interesting amongst them being CRL 40,238 (Example 2) and CRL 40,276 (Example 14) and above all CRL 40,271 (Example 10), which in addition to the anti-aggregation effect exhibits a hypo-lipidaemic action (total lipids: 35% inhibition) and hypo-cholesterolaemic action (cholesterol: 54% inhibition) at a dose of 0.1 g/kg in rats.

The results of the anti-aggregation test and of the hypo-lipidaemic action and hypo-cholesterolaemic action tests of other products of the invention have been lised in Table V which follows, the code used being the following (for each dose shown):
zero activity: −
significant activity: +
intense activity: + +
very intense activity: + + +

TABLE V

| Example | Code No. | Oral daily test dose in rats | Anti-aggregation action | Hypo-lipidaemic and hypo-cholesterolaemic action |
|---|---|---|---|---|
| 75 | CRL 40,253 | 10 mg/kg for 4 days | not tested | Total lipids : −40% Cholesterol : −40% |
| 19 | CRL 40,333 | 100 mg/kg for 4 days | + + | Total lipids : −24% Cholesterol : −20% |
| 23 | CRL 40,293 | 50 mg/kg for 3 days | + +(a) | Total lipids : −40% Cholesterol : −40% |
| 24 | CRL 40,310 | 100 mg/kg for 4 days | — | Total lipids : −20% Cholesterol : −32% |
| 25 | CRL 40,312 | 100 mg/kg for 4 days | + | — |
| 26 | CRL 40,282 | 100 mg/kg for 4 days | + | — |
| 27 | CRL 40,300 | 100 mg/kg for 4 days | + | — |
| 28 | CRL 40,332 | 100 mg/kg for 4 days | + | — |
| 29 | CRL 40,317 | 100 mg/kg for 4 days | + | Total lipids : −37% Cholesterol : −58% |
| 31 | CRL 40,295 | 100 mg/kg for 4 days | + + + | Total lipids : −19% Cholesterol : −32% |
| 31 | CRL 40,295 | 200 mg/kg for 4 days | + + + | Total lipids : −28% Cholesterol : −37% |
| 32 | CRL 40,330 | 100 mg/kg for 4 days | + | Total lipids : −13% Cholesterol : −13% |
| 37 | CRL 40,283 | 200 mg/kg for 4 days | + | not tested |
| 39 | CRL 40,334 | 100 mg/kg for 4 days | + + + | Total lipids : −17% Cholesterol : −17% |
| 42 | CRL 40,322 | 100 mg/kg for 4 days | + | — |

Note :
(a) : + + + at a dose of 100 mg/kg per day for 3 days

Some of the other results of the pharmacological tests which were carried out on rats are summarised below.

CRL 40,386 (product of Example 8)

Rats given a normal diet are treated orally at a daily dose of 50 mg/kg for 3 and 5 days. A reduction of about 20% in the concentration of cholesterol and lipids in the plasma is observed.

In another series of rats, a reduction of 26% in the cholesterol and of 42% in the total lipids in the plasma is achieved with 100 mg/kg given orally for 4 days.

CRL 40,387 (product of Example 59)

Rats given a normal diet are treated orally at a dose of 10 mg, 20 mg and 50 mg/kg for 3 and 5 days. It is found that the reduction in the cholesterol and in the lipids is about 25% for the 3 doses after the first 3 days' treatment.

It is furthermore observed that at the doses studied, CRL 40,387 has no effect on the blood platelet aggregation.

CRL 40,388 (product of Example 60)

It is found that there is a reduction of 33% in the lipids and of 18% in the cholesterol at doses of 50 and 100 mg/kg given orally, after 4 days' treatment.

CRL 40,389 (product of Example 61)

At a dose of 50 mg/kg given orally, a reduction of 35% in the lipids and of 35% in the cholesterol is found after 4 days' treatment.

CRL 40,390 (product of Example 62)

At a dose of 20 mg/kg given orally, a reduction of 25% in the lipids and in the cholesterol is found, and at doses of 50 mg/kg and 100 mg/kg reductions of 40% and 55%, respectively, are found in the lipids and the cholesterol after 4 days' treatment.

CRL 40,391 (product of Example 63)

At doses of 10, 20 and 50 mg/kg given orally for 3 to 5 days, it is found that the product acts as a hypo-lipidaemic and hypocholesterolaemic agent; at these doses, the reduction in the lipids is respectively 17, 21 and 29%, and that in the cholesterol respectively 32, 43 and 42%, after 3 days' treatment.

The anti-aggregation action was studied in accordance with two tests. At a dose of 100 mg/kg given orally for 4 days, it is found that according to the collagen test, the latency time is +40 and the speed is −32, whilst, according to the ADP test, the inhibition of transmission is 19%.

CRL 40,394 (product of Example 64)

The reduction in the cholesterol is 16 (?%) and that in the lipids is 33% after 5 days' treatment at a dose of 50 mg/kg.

CRL 40,395 (product of Example 65)

At a dose of 100 mg/kg given orally, the reduction in the cholesterol is 27% and that in the lipids is 18%, after 4 days' treatment.

CRL 40,398 (product of Example 66)

At a dose of 100 mg/kg given orally, the reduction in the lipids is 17% after 4 days' treatment. On the other hand, it is found that there is no change in the cholesterol content.

CRL 40,402 (product of Example 68)

At doses of 10 mg/kg, 20 mg/kg and 50 mg/kg given orally, a reduction in the cholesterol content and lipids content is observed after 3 to 5 days' treatment, in particular a reduction of 14% in the cholesterol and of 17% in the lipids at a dose of 20 mg/kg after 3 days' treatment.

Furthermore, it is found that the product has an anti-aggregation action according to the ADP test at a dose of 100 mg/kg given orally, the inhibition of transmission being 25% after 4 days' treatment.

CRL 40,403 (product of Example 69)

At a dose of 100 mg/kg given orally, a reduction of 32% in the cholesterol and of 10% in the lipids is observed after 4 days' treatment.

CRL 40,405 (product of Example 70)

At a dose of 100 mg/kg given orally, a reduction of 44% in the cholesterol and of 35% in the lipids is observed after 4 days' treatment. At a dose of 20 mg/kg the reduction in the cholesterol is 30% and that in the lipids is 12% after 5 days' treatment.

The product modifies the platelet aggregation according to the collagen test (latency time: +10; speed: −17; % transmission: −10%) at a dose of 100 mg/kg given for 4 days.

CRL 40,408 (product of Example 71)

At a dose of 100 mg/kg given orally, a reduction of 20% in the cholesterol and of 17% in the lipids is observed after 4 days' treatment.

CRL 40,409 (product of Example 72)

At a dose of 100 mg/kg given orally, a reduction of 9-10% in the lipids is observed after 4 days' treatment.

CRL 40,414 (product of Example 74)

At a dose of 100 mg/kg given orally, a reduction of 12% in the lipids is observed after 4 days' treatment.

The other pharmacological tests which have been carried out with CRL 40,293 (Example 23) have been listed below.

Toxicity

In female mice, the LD-50 on oral administration is 2,050 mg/kg. In male rats, the LD-0, on oral administration, is greater than 600 mg/kg.

It has furthermore been observed that CRL 40,293 is a well-tolerated substance. In fasting rats (a batch of 3 animals) which receive 1 g/kg of the product through a probang, no ulceration or inflammation of the stomach and of the duodenum is observed after killing the animals 8 hours after administration.

Cardio-vascular activity

Three anaesthetised dogs are used for this study. The product is administered intraduodenally as a gum suspension.

Two dogs with the thorax closed and respiring spontaneously are given CRL 40,293 at a dose of 100 mg/kg followed by 200 mg/kg, this second dose being administered 1 hour 30 minutes to 2 hours after the first. None of the parameters measured changed during the 2 hours' observation (arterial pressure, pulse rate, left intra-ventricular pressure, dp/dt, vertebral and femoral arterial flow rates and respiration).

One dog with the thorax opened is given 100 mg/kg, followed after 1 hour by 200 mg/kg, of CRL 40,293. None of the parameters measured changed during the 2 hours' observation (arterial pressure, pulse rate, left intraventricular pressure, dp/dt, aorta flow rate, work of the left ventricle, coronary arterial flow rate).

In these animals the effects of injections of noradrenalin, acetylcholine, tyramine, DMPP, histamine and serotonine were unchanged and the same is true of the effects of occlusion of the carotids and of stimulation of the central end and peripheral end of the vagus.

The product has a good hypo-lipidaemic and hypo-cholesterolaemic activity as indicated in Table V for an oral dose of 50 mg/kg. Furthermore, at a daily oral dose of 10 mg/kg the decrease in total lipids and in cholesterol is 20% after 3–4 days' treatment.

The clinical tests have made it possible to confirm the pharmacological tests. Thus, in man, CRL 40,293 (Example 23) in the form of gelatine-coated pills containing 400 mg of active ingredient administered at the rate of 2 such pills twice daily has given good results in the treatment of circulatory complaints and especially of lipid disturbances.

CRL 40,317 (Example 29) and CRL 40,295 (Example 31) each in the form of a tablet containing 250 to 500 mg of active ingredient, and administered to man to prevent cardiovascular accidents, were well tolerated, especially in the treatment of coronary insufficiency.

CRL 40,271 (Example 10) was well tolerated in man and has proved efficient in the treatment of circulatory complaints due to hyperlipidaemias when used in the form of a gelatine-coated pill containing 200 to 400 mg of active ingredient and taken at the rate of 1 to 2 such pills per day. CRL 40389 (Example 61) was well tolerated in man and has proved efficient in the treatment of hyperlipidaemia when used in the form of capsules or gelatine-coated pills each containing 500 mg of active ingredient and taken at the rate of 2 to 4 such capsules of pills per day.

CRL 40,386 (Example 8) has been used in man for the treatment of hyperlipidaemia in the form of gelatine-coated pills each containing 300 mg of active ingredient at the rate of 2 to 6 such pills per day.

CRL 40414 (Example 64) has been used with success in man for treating hyperlipidaemia in the form of gelatine-coated pills each containing 300 mg of active ingredient at the rate of 3 such pills per day.

We claim:

1. A sulphur-and-oxygen- containing compound of the formula

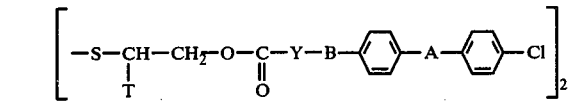

wherein n is an integer having a value of 5 to 15, T is H or $CH_3$, A is O, S, SO or $SO_2$, B is O, S, SO or $SO_2$, and Y is $CH_2$, $CH(CH_3)$ or $C(CH_3)_2$.

2. A compound according to claim 1, wherein n is 10, T is H or $CH_3$, A is O or S, B is O or S and Y is $CH_2$, $CH(CH_3)$ or $C(CH_3)_2$.

3. A compound according to claim 2, which is 3,14-diathia-1,16-hexadecyl di[4-(4-chlorophenylthio)-phenoxy- isobutyrate].

4. Therapeutic composition for reducing aggregation action of platelets containing a pharmaceutically effective amount of at least one compound according to claim 1 in combination with a physiologically acceptable excipient.

5. The method of treatment of cardiovascular diseases comprising administration to a human being of a pharmaceutically effective amount of the esters of claim 1.

* * * * *